(12) United States Patent
Mascari et al.

(10) Patent No.: US 11,612,143 B2
(45) Date of Patent: Mar. 28, 2023

(54) APPARATUS AND METHOD OF USING A SIMULATED SKIN SUBSTRATE FOR TESTING INSECT REPELLANTS

(71) Applicant: S. C. JOHNSON & SON, INC., Racine, WI (US)

(72) Inventors: Thomas Michael Mascari, Milwaukee, WI (US); Richard W. Wadleigh, Racine, WI (US)

(73) Assignee: S. C. JOHNSON & SON, INC., Racine, WI (US)

( * ) Notice: Subject to any disclaimer, the term of this patent is extended or adjusted under 35 U.S.C. 154(b) by 519 days.

(21) Appl. No.: 16/797,906

(22) Filed: Feb. 21, 2020

(65) Prior Publication Data

US 2020/0214267 A1   Jul. 9, 2020

Related U.S. Application Data

(62) Division of application No. 15/650,516, filed on Jul. 14, 2017, now Pat. No. 10,609,906.

(60) Provisional application No. 62/363,061, filed on Jul. 15, 2016.

(51) Int. Cl.
| | |
|---|---|
| *A01K 29/00* | (2006.01) |
| *A01M 1/02* | (2006.01) |
| *G01N 33/50* | (2006.01) |
| *A61L 27/60* | (2006.01) |
| *A01K 67/033* | (2006.01) |
| *A01M 29/12* | (2011.01) |

(52) U.S. Cl.
CPC .......... *A01K 29/005* (2013.01); *A01K 67/033* (2013.01); *A01M 1/023* (2013.01); *A01M 29/12* (2013.01); *A61L 27/60* (2013.01); *G01N 33/5088* (2013.01); *A61B 2503/42* (2013.01); *G01N 2333/43591* (2013.01)

(58) Field of Classification Search
None
See application file for complete search history.

(56) References Cited

U.S. PATENT DOCUMENTS

| | | | |
|---|---|---|---|
| 3,572,131 | A | 3/1971 | Wright et al. |
| 4,168,591 | A | 9/1979 | Shaw |
| 5,091,423 | A | 2/1992 | Wilson et al. |
| 6,088,949 | A | 7/2000 | Nicosia et al. |
| 6,165,449 | A | 12/2000 | George et al. |
| 6,660,288 | B1 | 12/2003 | Behan et al. |
| 6,953,814 | B2 | 10/2005 | Reifenrath |
| 7,579,016 | B2 | 8/2009 | Zhang et al. |
| 2006/0082773 | A1 | 4/2006 | Sottery et al. |
| 2006/0260183 | A1 | 11/2006 | Hockaday |
| 2006/0260548 | A1 | 11/2006 | Palomino et al. |
| 2008/0059218 | A1 | 3/2008 | Sottery et al. |
| 2009/0313883 | A1 | 12/2009 | Olson et al. |
| 2012/0124890 | A1 | 5/2012 | Hainze |
| 2015/0216164 | A1 | 8/2015 | Bedoukian et al. |
| 2015/0320039 | A1 | 11/2015 | Emmrich et al. |
| 2017/0319466 | A1 | 11/2017 | Murray et al. |

FOREIGN PATENT DOCUMENTS

| | | |
|---|---|---|
| WO | 1996008147 A2 | 3/1996 |
| WO | 2012068506 A1 | 5/2012 |
| WO | 2013165479 A1 | 11/2013 |
| WO | 2015063238 A1 | 5/2015 |

OTHER PUBLICATIONS

Ali et al. "A New In Vitro Bioassay System for the Discovery and Quantitative Evaluation of Mosquito Repellents" Journal of Medical Entomology, 2017, 9 pages.
Damiens et al. "Different Blood and Sugar Feeding Regimes Affect the Productivity of *Anopheles arabiensis* Colonies (Diptera: Culicidae)" Journal of Medical Entomology. 2013. 21 pages.
Deng et al. "A novel mosquito feeding system for routine blood-feeding of *Aedes aegypti* and *Aedes albopictus*" Tropical Biomedicine 29 (1) 2012. 6 Pages.
Grieco et al. "A Novel High-Throughput Screen System to Evaluate the Behavioral Response of Adult Mosquitoes to Chemicals" Journal of the American Mosquito Control Association, 2005, 8 pages.
Klun et al. "A New In Vitro Bioassay System for Discovery of Novel Human Use Mosquito Repellents" Journal of the American Mosquito Control Association, 2005, 8 pages.
Krober "An In Vitro Assay for Testing Mosquito Repellents Employing a Warm Body and Carbon Dioxide as a Behavioral Activator" Journal of the American Mosquito Control Association, 26(4):381-386. 2010, 7 pages.
Luo "A novel multiple membrane blood-feeding system for investigating and maintaining *Aedes aegypti* and *Aedes albopictus* mosquitoes" Journal of Vector Ecology vol. 39 No. 2 Dec. 2014, 7 pages.
Mayer et al. "Attraction of *Aedes aegypti* (L.): responses to human arms, carbon dioxide, and air currents in a new type of olfactometer1" Bulletin of Entomological Research, vol. 58 / Issue 03 / Feb. 1969, 1 page.
Menger et al. "Assessing the efficacy of candidate mosquito repellents against the background of an attractive source that mimics a human host" The Royal Entomological Society, May 6, 2014, 1 page.
Rehman et al. "A Novel in vitro Bioassay to Explore the Repellent Effects of Compounds Against Mosquito *Aedes aegypti* (Diptera: Culicidae)", Journal of Medical Entomology, Nov. 20, 2015, 10 pages.
Ricciuti "Researchers Develop Improved Lab-Testing System for Mosquito Repellents", Entomology Today, Jun. 5, 2017, 5 pages.

(Continued)

*Primary Examiner* — Robert J Yamasaki
(74) *Attorney, Agent, or Firm* — Quarles & Brady LLP

(57) ABSTRACT

An apparatus includes a housing having an aperture extending through a wall of the housing, a carbon dioxide delivery device coupled to the housing through the aperture, a non-biological skin substitute substrate, and a heater coupled to the substrate.

5 Claims, 20 Drawing Sheets

(56) References Cited

OTHER PUBLICATIONS

Sattabongkot et al. "Comparison of artificial membrane feeding with direct skin feeding to estimate the infectiousness of plasmodium vivax gametocyte carriers to mosquitoes" The American Society of Tropical Medicine and Hygiene, 2003, 7 pages.
Verhulst et al. "Cultured Skin Microbiota Attracts Malaria Mosquitoes" Malaria Journal, Dec. 17, 2009, 12 pages.
"Feeding System" Commerce Business Daily. Jun. 24, 2015, 1 page.
International Search Report and Written Opinion for International Application No. PCT/US2017/042187, dated Oct. 9, 2017, 14 pages.
Schreck, C.E., "Techniques for the Evaluation of Insect Repellents: A Critical Review" Ann. Rev. Entomol. vol. 22: 101-19 (1977) (Year: 1977).

APPARATUS AND METHOD OF USING A SIMULATED SKIN SUBSTRATE FOR TESTING INSECT REPELLANTS

CROSS REFERENCE TO RELATED APPLICATIONS

This application is a divisional of U.S. patent application Ser. No. 15/650,516, filed Jul. 14, 2017, which claims priority to U.S. Provisional Patent Application No. 62/363,061, filed on Jul. 15, 2016, each of which is incorporated herein by reference as if set forth in its entirety.

REFERENCE REGARDING FEDERALLY SPONSORED RESEARCH OR DEVELOPMENT

Not applicable

SEQUENCE LISTING

Not applicable

BACKGROUND OF THE INVENTION

1. Field of the Invention

The present disclosure generally relates to an apparatus for evaluating the effectiveness of insect repellents on human skin using a simulated skin substrate and methods for using same. The method is particularly useful and suitable for testing the efficacy of skin-applied insect repellents and the attraction of biting insects to human subjects without using human testing participants.

2. Description of the Background of the Invention

Insect-transmitted diseases have long been prevalent, however there are significant hurdles to the development of new effective insect repellents because of the difficulties of testing the efficacy of those new repellents. Particularly, the testing of skin-applied insect repellents and the attraction of biting insects to human subjects is difficult to test without using human test subjects.

Efficacy tests without using human subjects have many benefits. In general, tests involving human subjects tend to have higher operational costs and complicated testing protocols. When human subjects are not employed in tests, experimental costs can be reduced significantly. Further, tests using human surrogate apparatuses can be conducted without geographic or environmental limitations. Particularly, similar tests can be conducted in multiple environments, e.g., a temperate or tropical zone, to reduce the number of variables except for those unique to each geographic locale. All of these benefits assist in making improved repellents based on the location of the consumer.

A need exists for human surrogate testing apparatuses and methods for determining the effectiveness of insect repellents. Several previously developed tests involve using a collagen membrane or a piece of fabric over a warmed feeding chamber containing blood, artificial blood, or warm water containing stimulants for insects. However, these tests and methods do not provide comparable testing results to those derived from tests involving human subjects, and collagen-based substrates do not permit repeated testing cycles. Therefore, it is important to develop a human surrogate apparatus and method for testing the effectiveness of insect repellents using a non-collagen based substrate, which provides identical or substantially similar results to tests involving human participants without having the limitations associated with collagen substrates.

SUMMARY OF THE INVENTION

The present disclosure presents methods and apparatuses for testing the efficacy of skin-applied repellents by employing a simulated human non-collagen based skin substrate. In certain embodiments, a method for testing the efficacy of skin-applied insect repellents comprises the steps of providing a skin substitute substrate, exposing biting insects to the skin substitute substrate treated with an insect repellent, blocking the treated skin substitute substrate from the plurality of insects for a second period of time, repeating the exposing step and the blocking step for (n) times until at least one insect lands on the treated skin substitute substrate for greater than a third period of time during the (n) exposure step and during a subsequent (n+1) exposure step, and recording a complete protection time ("CPT").

In certain embodiments a method for testing the efficacy of a skin-applied insect repellent comprises the steps of providing a non-biological skin substitute substrate simulating at least one physical, chemical, or biological characteristic of human skin, treating the skin substitute substrate with an insect repellent, exposing a plurality of insects to the treated skin substitute substrate for a first period of time, blocking the treated skin substitute substrate from the plurality of insects for a second period of time, repeating the exposing step and the blocking step for (n) times until at least one insect lands on the treated skin substitute substrate for greater than a third period of time during the (n)th exposure step and during a subsequent (n+1)th exposure step, and recording a fourth period of time needed to reach the (n)th exposure. In certain embodiments the method comprises the step of enclosing the treated skin substitute substrate and the plurality of insects in a housing. In certain embodiments the non-biological skin substitute substrate is synthetic.

In certain embodiments the non-biological skin substitute substrate has an $R_a$ value of about 0.01 to about 0.2 μm. In certain embodiments the non-biological skin substitute substrate has specular reflectance peak at a wavelength of about 306 nm. In certain embodiments the non-biological skin substitute substrate has a diffuse reflectance exhibiting properties associated with a Lambertian reflectance. In certain embodiments the contact angle between the insect repellent and a surface of the non-biological skin substitute substrate approaches or is substantially zero.

In certain embodiments, the treated non-biological skin substitute substrate is exposed to biting insects for about 1 minute to about 5 minutes and withdrawn from biting insects for about 25 minutes to about 29 minutes. In one particular embodiment, the treated skin substitute substrate is exposed to biting insects for about 1 minute and withdrawn from biting insects for about 29 minutes. This cycle is repeated until one or more biting insects land on the treated substrate for equal to or longer than 2 seconds. If in the subsequent exposure, one or more biting insects land on the treated substrate again for equal to or longer than 2 seconds, the repeated cycle is terminated and the last exposure time is the CPT of the tested repellent. Collagen-based substrates cannot be used in assays comprising multiple testing cycles.

In some embodiments, additional steps of the method may include providing a housing comprising a plurality of insects, supplying the housing with carbon dioxide ($CO_2$) at a rate of about 400 mL/min (14 oz/min) to about 600 mL/min (20.3 oz/min), applying an amount of skin-applied insect repellent to the skin substitute substrate to form the treated substrate, and maintaining a temperature of the skin substitute substrate within a range of about 35° C. to about 39° C. Further, in some embodiments the additional steps of the method may comprise the step of placing the housing with the plurality of insects under a testing condition for about 30 minutes to acclimate the plurality of insects to the testing condition.

In certain embodiments, a method for testing the efficacy of skin-applied insect repellents comprises the steps of providing a synthetic, non-biological skin substitute substrate, treating the synthetic, non-biological skin substitute substrate with an insect repellent, exposing a plurality of insects to the treated skin substitute substrate for a first period of time, blocking the treated skin substitute substrate from the plurality of insects for a second period of time, repeating the exposing step and the blocking step for (n) times until at least one insect lands on the treated skin substitute substrate for greater than a third period of time during the (n)th exposure step and during a subsequent (n+1)th exposure step, and recording a fourth period of time needed to reach the (n)th exposure, wherein the treated skin substitute substrate and the plurality of insects are enclosed in a housing.

Certain embodiments of the method for testing the efficacy of skin-applied insect repellents comprises exposing the plurality of insects in the housing to an untreated skin substitute substrate for about 60 seconds, recording the number of insects that land on the untreated substrate for longer than about 2 seconds, and determining whether the plurality of insects in the housing need to be replaced, wherein the determination to replace occurs when the recorded number of insects that land is less than 20.

In other embodiments, a human surrogate apparatus for testing the efficacy of skin-applied repellents is disclosed. In certain embodiments the apparatus for testing the efficacy of a skin-applied insect repellent comprises a housing comprising an aperture extending through a wall of the housing, a carbon dioxide delivery device coupled to the housing through the aperture, a non-biological skin substitute substrate, and a heater coupled to the non-biological skin substitute substrate. In certain embodiments the non-biological skin substitute substrate simulates at least one physical, chemical, or biological characteristic of human skin. In certain embodiments the non-biological skin substitute is synthetic. Further, when the housing is open, insects within the housing will have access to the skin substitute substrate; and when the housing is closed, the insects will not have access to the skin substitute substrate.

In certain embodiments, the non-biological skin substitute substrate has an $R_a$ value of about 0.01 to about 0.2 µm. In certain embodiments the non-biological skin substitute substrate has specular reflectance peak at a wavelength of about 306 nm. In certain embodiments the non-biological skin substitute substrate has a diffuse reflectance exhibiting properties associated with a Lambertian reflectance. In certain embodiments the contact angle between the insect repellent and a surface of the non-biological skin substitute substrate approaches or is substantially zero.

In certain embodiments, a portable human surrogate apparatus for field testing the efficacy of skin-applied repellents is disclosed. An embodiment of the portable human surrogate apparatus comprises a portable housing with a cavity, a heater disposed within the cavity of the housing, a temperature buffering device coupled to the heater and disposed within the cavity of the housing, a non-biological skin substitute substrate coupled to the temperature buffering device and disposed within the cavity of the housing, and a carbon dioxide delivery device coupled to the housing.

In certain embodiments, a method for measuring mosquito landing pressure is disclosed. An embodiment of the method comprises providing a non-biological skin substitute substrate, exposing a plurality of mosquitos to the skin substrate, and recording a number of mosquitos landing on the skin substrate during a period of time.

BRIEF DESCRIPTION OF THE DRAWINGS

Other aspects and advantages of the present invention will become apparent upon consideration of the following detailed description, wherein similar structures have similar reference numerals.

DETAILED DESCRIPTION

Embodiments of the current technology disclose human surrogate apparatuses and methods for using human surrogate apparatuses for conducting insect repellent evaluation tests. The disclosed human surrogate apparatuses and methods provide identical or substantially similar results to tests involving human participants for testing the effectiveness of an insect repellent without the limitations associated with collagen-based simulated skin substrates. Further, the human surrogate apparatuses according to an embodiment of the present disclosure are able to capture more mosquitoes compared to industry-standard mosquito traps.

Figure 1:
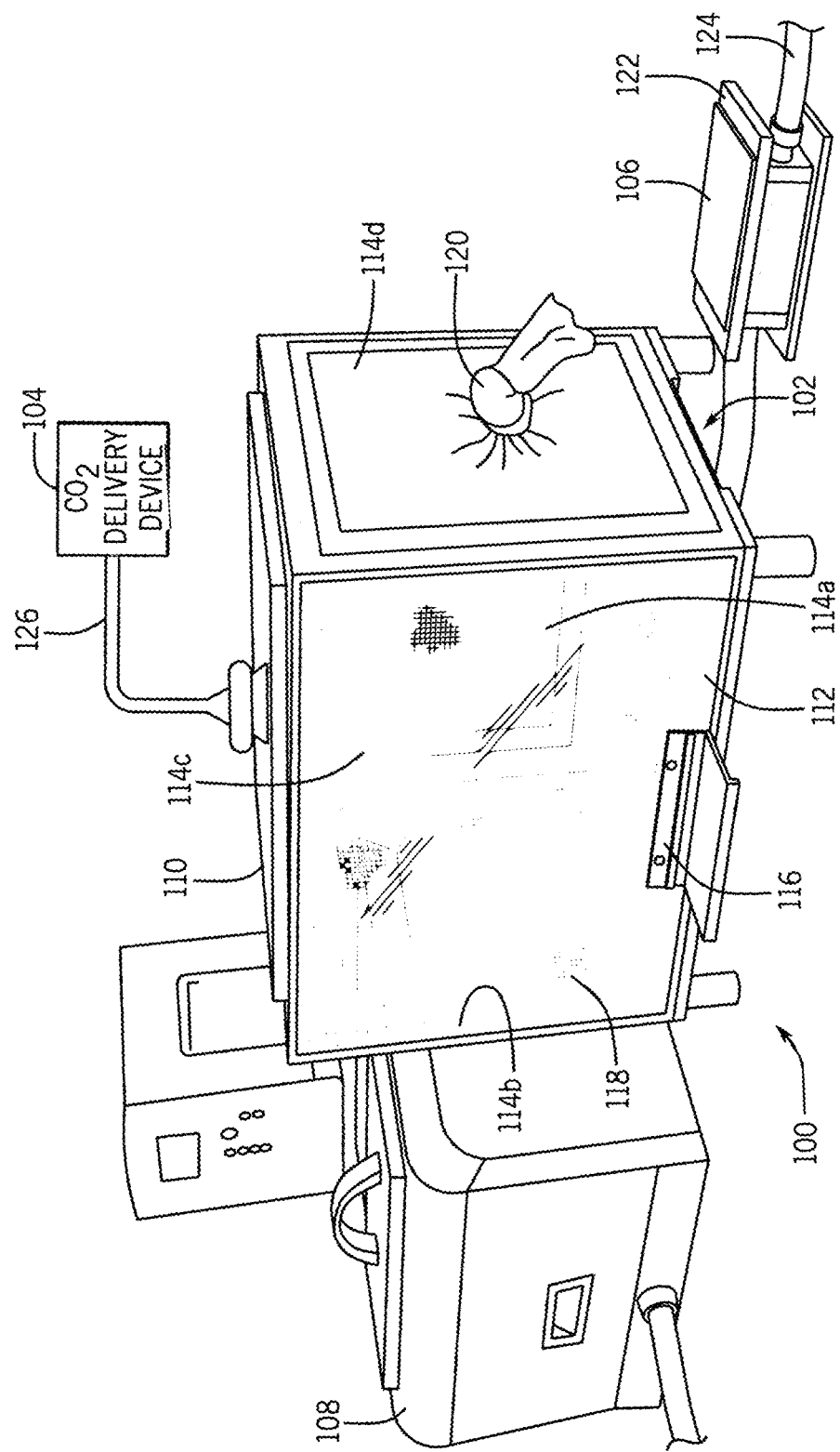
FIG. 1 illustrates an embodiment of a human surrogate apparatus for testing the effectiveness of insect repellents.

FIG. 1 illustrates one embodiment of a human surrogate apparatus 100 for testing the efficacy of a skin-applied insect repellent. The human surrogate apparatus 100 generally comprises a housing 102 for housing insects, a carbon dioxide delivery device 104, a non-collagen based, non-biological substrate 106, and a heater 108. The non-collagen based, non-biological substrate 106 may be synthetic.

In an embodiment, housing 102 is a framed and cuboid shaped cage with a storage volume defined by a width of about 18 inches, a depth of about 12 inches, and a height of about 12 inches. As described herein, "about" is used to mean a difference of plus or minus 10% in dimension measurements. In this embodiment, the described dimensions define a storage volume of about 2592 cubic inches, which allows housing 102 to house at least 200 biting insects, such as lab-reared mosquitoes, such as Aedes aegypti, during a testing. In other embodiments, the storage volume may be at least 1000 cubic inches, or at least 2000 cubic inches, or at least 2500 cubic inches. In yet other embodiments, the storage volume is sufficient to hold at least 100 mosquitoes, or at least 200 mosquitoes, or at least 500 mosquitoes. Further, housing 102 may comprise any shape insofar as it provides for a storage volume sufficient to hold a desired number of insects.

The construction of housing 102 may be varied based on numerous user considerations. In a preferred embodiment, housing 102 includes a top wall 110, a bottom wall 112, and side walls 114a-d. In the embodiment depicted in FIG. 1, the top wall 110 and the side walls 114a-d comprise a polycarbonate material, or other clear plastic or glass material. The bottom wall 112 comprises an opaque plastic or other material and includes a sliding door 116. It is further contemplated that the sliding door 116 may be any type of door or resealable opening and positioned on one or more of the walls 110, 112, 114a-d of housing 102. In the depicted embodiment, the side walls 114b and 114c include a mesh material 118 extending across a portion thereof, providing for fluid communication between the internal storage volume and the external atmosphere. More specifically, the mesh material may allow for air exchange and prevent $CO_2$ buildup in housing 102. Further, the side wall 114d includes a portion thereof comprising a fabric material 120, such as, for example, a material found in a typical orthopedic tubular stockinet. The fabric material 120 can provide an opening through which mosquitoes are placed in, or removed from, housing 102.

The substrate 106 is shown mounted to a disk 122, which is made of material that is able to transmit heat from a water tube 124 to the substrate 106. The disk 122 may comprise any shape, but preferably comprises a shape that corresponds to that of the sliding door 116 and that may be fittingly and/or sealingly received with and/or into an aperture defined by the sliding door. During testing, the disk 122 is positioned next to the sliding door 116 with the substrate 106 disposed on a surface of the disk. Because of the complementary shaping and sizing of the sliding door 116 and the disk 122, the substrate 106 is sealingly received within the housing 102 (or adjacent to the housing 102) to prevent biting insects from traveling outside the container.

With reference still to the illustrated embodiment of FIG. 1, the $CO_2$ delivery device 104 delivers $CO_2$ through a tube 126 into the container 102. The $CO_2$ delivery device 104 includes (or is in communication with) a pressurized source of $CO_2$, such as a pressurized $CO_2$ tank. In the present embodiment, the $CO_2$ is delivered at a constant rate of between about 400 mL/min (14 oz/min) to about 600 mL/min (20.3 oz/min). In other embodiments, the rate of $CO_2$ delivery may be provided in discrete pulses, e.g., mimicking the temporal duration of human breathing. Other ranges of pulse or constant $CO_2$ flow rates are contemplated that provide a periodic or constant flow of $CO_2$ within container 102 of between about 500 to about 1500 parts per million (ppm) to stimulate the mosquitoes during testing.

Moreover, in the depicted embodiment, heater 108 is a circulating water heater and maintains the temperature of the substrate 106 during testing at about 35° C. to about 39° C. In alternative embodiments, other temperatures are contemplated to simulate human conditions in varying environments. Warming the substrate 106 provides the benefit of stimulating mosquitoes during testing. The circulating water heater 108 contains a digital control for setting different temperatures and a water tube 124 extending from the heater 108 and running underneath the disk 122 and the substrate 106 to keep the substrate warm. It is further contemplated that any type of heater or heating system may be used to warm substrate 106 to about 35° C. to about 39° C. or any other desired temperature or temperature range.

Figure 2:
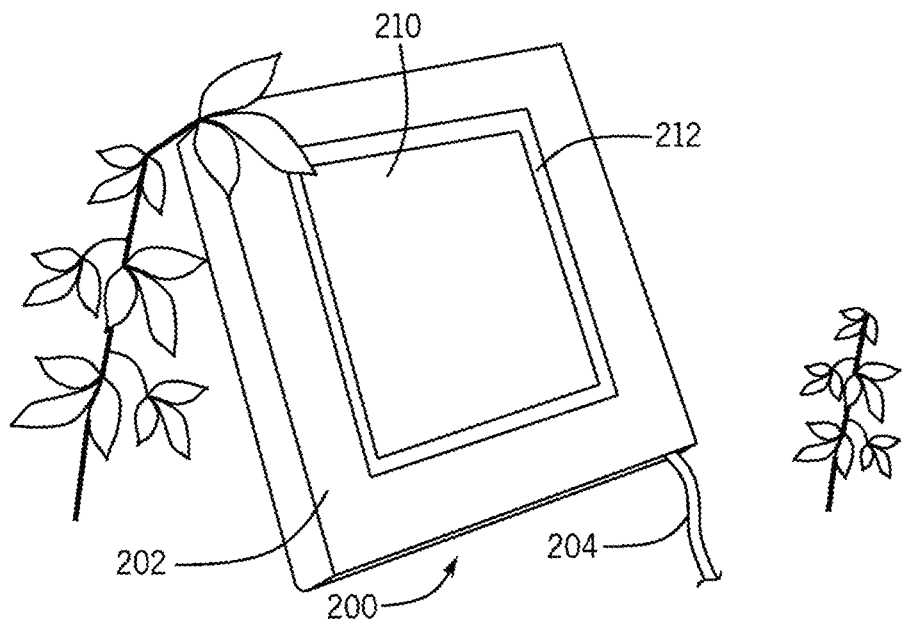
FIG. 2 demonstrates an embodiment of a field-portable human surrogate apparatus for testing the effectiveness of insect repellents.
Figure 3:
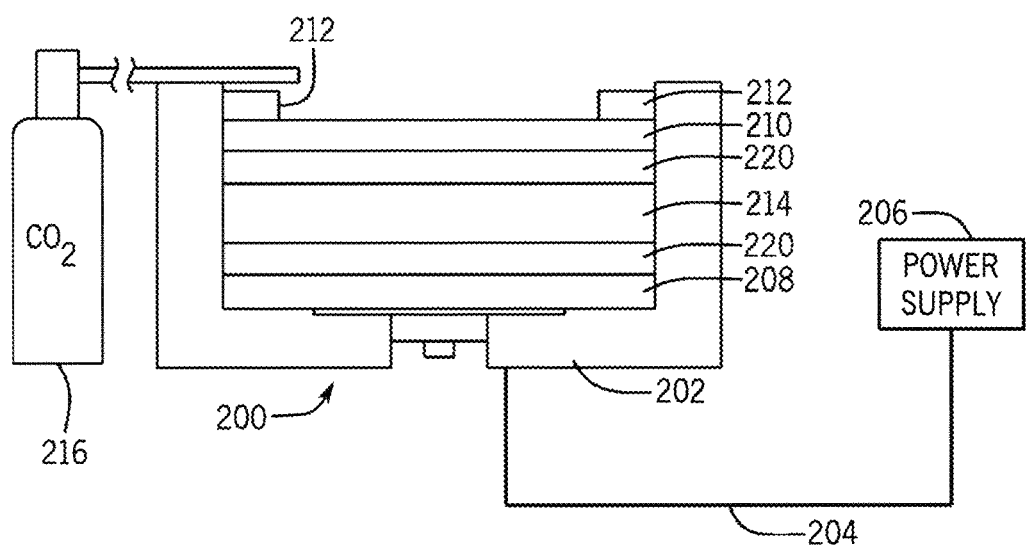
FIG. 3 is a schematic cutaway view illustrating components of the field-portable human surrogate apparatus of FIG. 2.

The human surrogate apparatus of FIG. 1 is intended for use in a laboratory or controlled environment. Preferably, the controlled environment has a temperature range of between about 24° C. to about 30° C. and a range of relative humidity of between about 40% to about 60%. In contrast, FIGS. 2 and 3 illustrate an embodiment of a human surrogate apparatus 200 for testing the efficacy of a skin-applied insect repellent in the field. By fashioning the human surrogate apparatus 200 to be portable, the apparatus may be used in any number of real world environments. The human surrogate apparatus 200 therefore provides the advantage of similar testing efficacy as human testing, but without exposure to mosquitoes or other insects found in the field.

With reference still to FIGS. 2 and 3, the human surrogate apparatus 200 is disposed in an outdoor environment, with an identified population of biting insects. The portable human surrogate apparatus 200 is provided with a housing 202 having a power supply line 204 connected thereto. In some embodiments, a power supply 206 is located remotely from the housing 202 to provide power to the human surrogate apparatus 200. Alternatively, or in addition, a local power supply is provided within or attached to the housing 202. In such an embodiment, the power supply line 204 may be omitted, provided within the housing 202, or otherwise fashioned differently within the housing 202 to allow energy to reach electrical components thereof.

With reference to FIG. 3, the human surrogate apparatus 200 includes a heater 208 in electrical communication with the power supply 206. In the present embodiment, the heater 208 is a silicone-rubber heating blanket, manufactured by BriskHeat Corporation, Columbus, Ohio. A non-collagen based, non-biological substrate 210 is also provided and is exposed to the ambient environment. In certain embodiments the non-collagen based, non-biological substrate 210 may be synthetic.

In the present embodiment, the substrate 210 is securely fastened to the portable human surrogate apparatus 200 by magnetic strips 212, or may be fastened by any other suitable means. In some embodiments a temperature buffering device 214 is provided beneath the substrate 210, which assists in transmitting heat from the heater 208 and maintains the substrate 210 at a predetermined temperature. In the present embodiment, the temperature buffering device 214 is a water bath, enclosed in a container 220, which is made of materials that prevent water leakage and that transmit heat at the same time. Moreover, the portable human surrogate apparatus 200 is connected to a $CO_2$ source 216, which may be remote from the housing 202, attached to the housing 202, or otherwise retained within the housing 202. In the present embodiment, the $CO_2$ source 216 delivers $CO_2$ at a rate of between about 400 mL/min (14 oz/min) to about 600 mL/min (20.3 oz/min).

In certain embodiments, the substrate used for both the laboratory and field testing is a skin substitute substrate. In some embodiments the skin substitute substrate is a non-biological testing substrate with surface properties similar to those of human skin. In some embodiments the skin substitute substrate is synthetic. In some embodiments the skin substitute substrate simulates, i.e., exhibits the same or substantially similar properties, of human skin in various aspects. Such simulated aspects include one or more of the mechanical, optical, thermal, electrical, chemical, or surface properties of human skin, such as surface roughness, surface optical reflection, and surface wetting ability. In some embodiments, one or more, or two or more, or three or more, or four or more, or five or more, or all of these attributes, are found in the substrates 106, 210. The non-biological, non-collagen-based substrate according to an embodiment of the present disclosure may be used in a multi-cycle testing method, wherein collagen based substrates cannot.

Numerous potential substrates exist that can simulate a human test subject, of which one or more of them may be taken singly or in combination to effect the purposes of the disclosed human surrogate apparatuses 100, 200. For example, various liquid suspensions can be used to simulate scattering and absorption properties of the skin. Particularly, gelatinous substances are used to simulate various physical, mechanical, and chemical properties, such as the elastic modulus, hardness, optical, or surface properties of the skin. Representative gelatinous substances used in the production of skin substitutes are gelatine, agar and agarose, collagens, and polyvinyl alcohol gels. Gelatine provides a matrix of density, stiffness, sound speed, absorption, and light scattering similar to that of human skin.

Further, elastomers can be used in making artificial skin substrates. Elastomers are polymers exhibiting rubber-like viscoelastic properties. Elastomers comprise a broad spectrum of natural and synthetic materials, inter alia silicones, polyurethanes, polyether block amides, polyisoprene, and polybutadiene. Specifically, silicone elastomers such as cross-linked polydimethylsiloxanes are suitable to generate skin substitute substrates.

Moreover, epoxy resins, which have a thermal diffusivity of between about 0.070 to about 0.084 $mm^2/s$ ($1\times10^{-4}$-$1.3\times 10^{-4}$ $inches^2/s$), which is close to that of human skin, make them another suitable choice for skin substitute substrates.

In some embodiments the skin substitute substrate is a synthetic (non-biological) testing substrate. In some embodiments, the substrate used for both laboratory and field testing is a synthetic (non-biological) testing substrate. In some embodiments the skin substitute substrate has a critical surface tension and ionic force identical, or substantially similar to, human skin. The substrate is non-collagen based, e.g., the substrate is not a collagen membrane. In one embodiment as illustrated herein, the skin substitute is a Vitro-Skin® substrate (manufactured by IMS, Inc., Portland, Me.), In certain embodiments, the skin substitute substrate comprises the following characteristics. For example, surface topography in terms of surface roughness was evaluated in the skin substitute substrate. Surface roughness, often shortened to roughness, is a component of surface texture. It is quantified by the deviations in the direction of the normal vector of a real surface from its ideal form. If these deviations are large, the surface is considered rough; if they are small, the surface is considered smooth. Moreover, roughness plays an important role in determining how a real object will interact with its environment. $R_a$ is the most commonly used roughness parameter. $R_a$ is calculated as the Roughness Average of a surface's measured microscopic peaks and valleys. $R_a$ is the arithmetic average of the absolute values of the profile height deviations from the mean line, recorded within the evaluation length. In other words, $R_a$ is the average of a set of individual measurements of a surface's peaks and valleys. The reported surface roughness values of human skin on certain body parts varies in the range $R_a$=0.03 through 0.45 μm. In case of very rough surfaces, up to $R_a$=90 μm (Hendrik, C. P. and Franklin, S. E., Influence of Surface Roughness, Material and Climate Conditions on the Friction of Human Skin. Tribology Letter (2010) Vol. 37, Issue 2, pp 361-373.) In certain embodiments the $R_a$ value of the skin substitute substrate according to the present disclosure was about 0.10±0.07 μm (n=7), which is within the range of surface roughness values of human skin. $R_a$ measurements were made using a Starrett SR300 surface roughness meter (manufactured by the L.S. Starrett Company, Athol, Mass.).

Figure 9A:
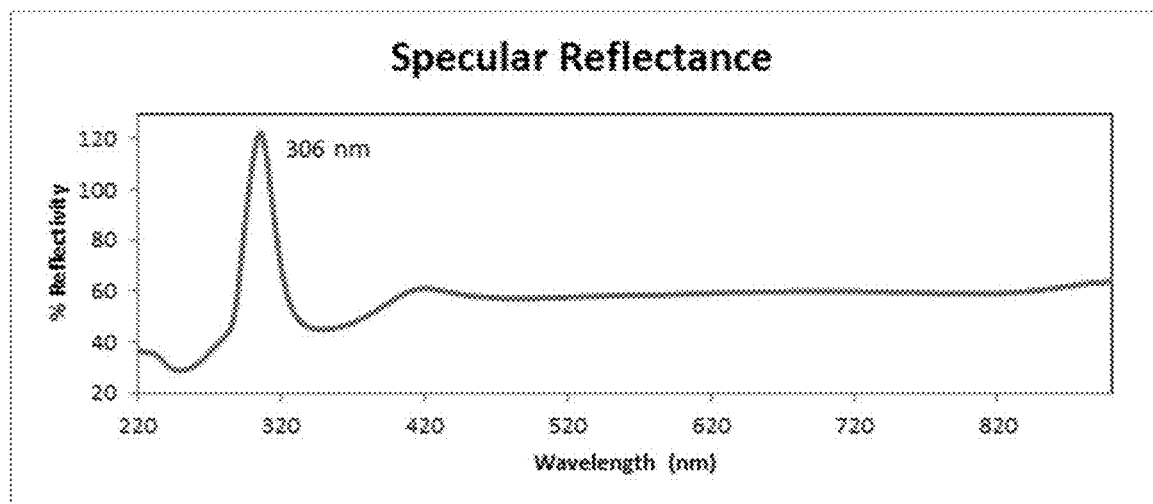
FIGS. 9A and 9B illustrate the specular reflectance and diffuse reflectance of the synthetic (non-biological) skin substitute substrate, namely, in this example, Vitro-Skin®.
Figure 9B:
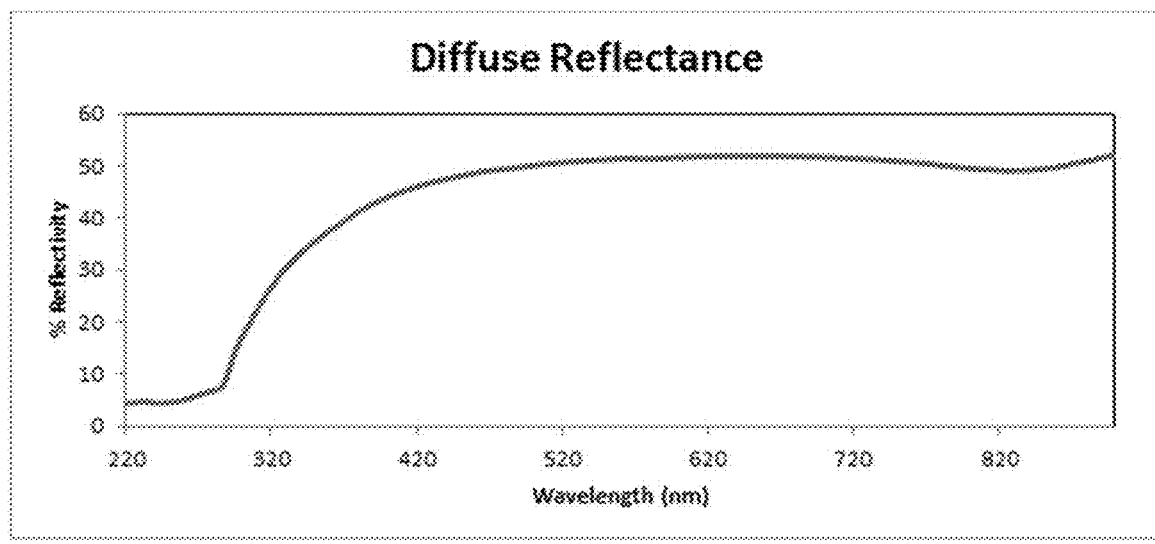

Further, the surface topography of the skin substitute substrate was characterized by measuring its wavelength dependent optical reflection. The optical reflection was determined using a Shimadzu UV-2600 UV-Vis Spectrophotometer (manufactured by Shimadzu Scientific Instruments, Inc., Columbia, Md.) and the results were demonstrated in specular reflectance (FIG. 9A) and diffuse reflectance (FIG. 9B). Specular reflection, also known as regular reflection is the mirror-like reflection of waves, such as light, from a surface. In this process, each incident ray is reflected, with the reflected ray having the same angle to the surface normal as the incident ray. Diffuse reflection is the reflection of light from a surface such that an incident ray is reflected at many angles rather than at just one angle as in the case of specular reflection. An illuminated ideal diffuse reflecting surface will have equal luminance from all directions which lie in the half-space adjacent to the surface (Lambertian reflectance). Referring to FIG. 9A, a specular reflectance peak of the skin substitute substrate was identified at a wavelength of 306 nm. Referring to FIG. 9B, the diffuse reflectance exhibited the properties associated with a Lambertian reflectance.

Additionally, the surface wetting of insect repellents on the skin substitute substrate should be close to the surface wetting of insect repellents on human skin. The term "wetting" refers to the ease with which a substance can intimately contact and spread over a given substrate. There are a variety of forces (ionic, static, polar, van der Waals etc.) acting between the substance and the substrates that ensure good bonding. Good wetting provides a larger area of contact where these forces may act. Consequently, good wetting is crucial for good bond formation. Insect repellant actives, such as para-menthane-3,8-diol (PMD), DEET, and 2-(2-hydroxyethyl)-1-piperidinecarboxylic acid 1-methylpropyl ester (picaridin), were tested on a hydrated skin substitute substrate where substantially complete wetting was observed, similar to testing on human skin. Complete wetting is achieved when the contact angle between the liquid and the solid surface is approaching or is substantially zero. Also, substantially complete wetting demonstrates favorable interactions between the active substance and the tested skin substitute substrate. The interaction of ethanol solutions containing 5%, 10%, 15%, and 25% of each aforementioned active substance and the tested skin substitute substrate was also tested. Again, substantially complete wetting was observed for each tested ethanol solution on the tested skin substitute substrate. Due to this degree of wetting between the insect repellent active and the tested skin substitute substrate, the desired bonding between the active and the tested skin substitute substrate is achieved. As a result, the insect repellent remains on the skin substitute substrate for a duration similar to that of human skin.

Figure 4:
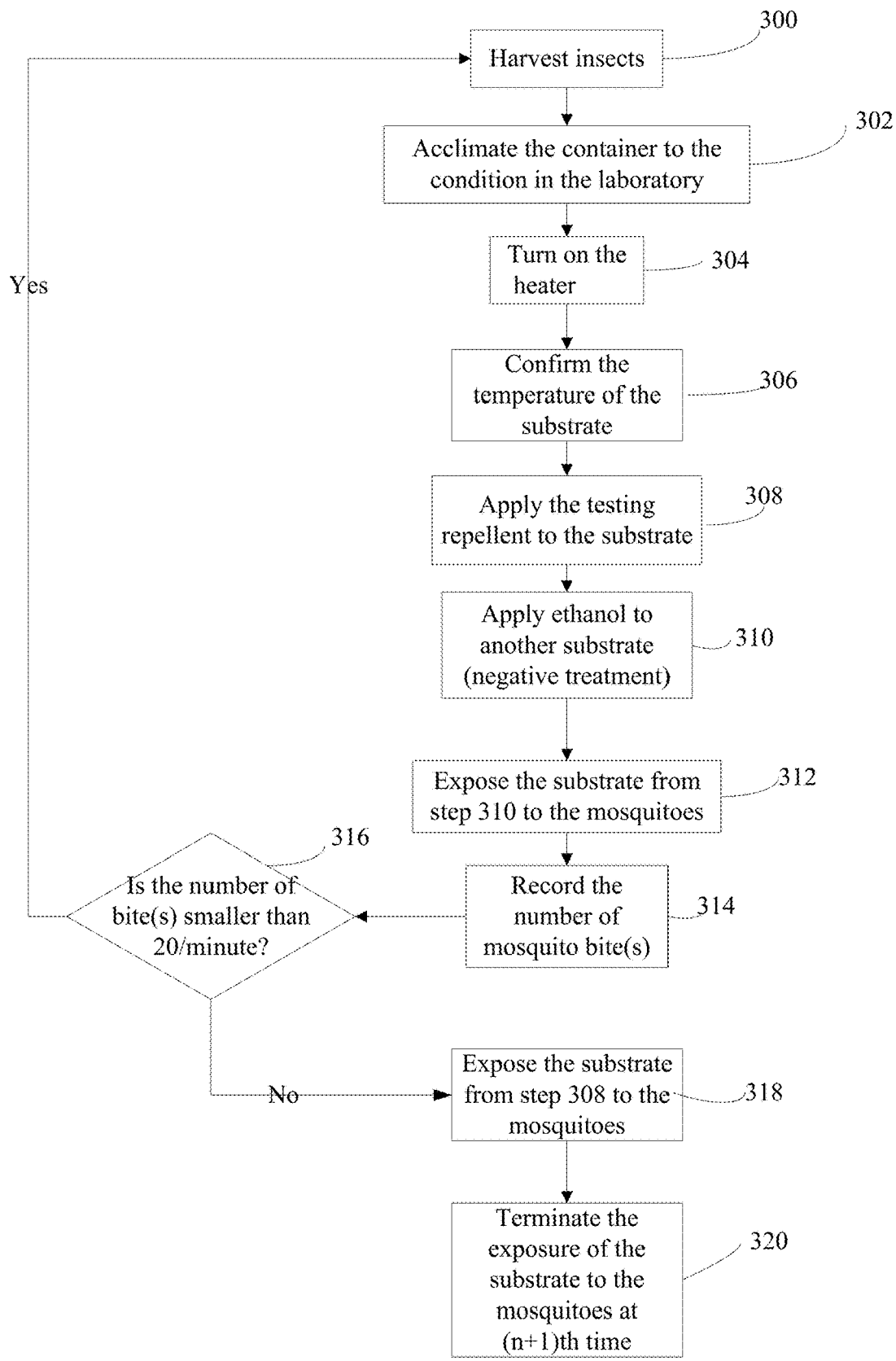
FIG. 4 is a flowchart illustrating the method of using the human surrogate apparatus of FIGS. 1 and 2 to test the efficacy of an insect repellent.

With reference to FIG. 4, a method of using the human surrogate apparatus 100 is explained. Further, data from using this method will provide experimental evidence of the efficacy of the use of the human surrogate apparatus 100 in view of other conventional techniques. At step 300, approximately 200 adult female mosquitoes are extracted from an insectary cage and are transferred to the container 102. In step 302, the container 102 is placed in the testing room under a particular condition for about 30 minutes to acclimate the mosquitoes to the predetermined testing condition. For example, the predetermined testing condition of the present embodiment has a temperature range of between about 24° C. to about 30° C. and a range of relative humidity of between about 40% to about 60%. Further, in step 304, the heater 108 is turned on and the temperature set to between about 24° C. to about 30° C., warming substrate 106. In the present embodiment, substrate 106 comprises Vitro-Skin®. The surface temperature of substrate 106 is further confirmed at step 306 to be at the predetermined level, e.g., by a laser thermometer or any other thermometer that is capable of measuring surface temperature.

Upon the determination that the appropriate temperature of substrate 106 has been reached, a test substance, which can be applied on skin, containing insect repellent is applied to substrate 106 at step 308. In certain embodiments, different test substances contain different concentrations of testing insect repellent. The concentration of testing insect repellent can be measured by weight percentage or by volume percentage of the testing insect repellent diluted in ethanol or in any other suitable diluents. In the present embodiment, about 0.19 g of skin-applied test substance, i.e., the combined mass of the repellent and diluent, is applied to the warmed substrate during step 308. Further, in the present embodiment, regardless of the concentration of the repellent, the combined mass of the repellent and ethanol is about 0.19 g. In other experiments, the combined mass of the repellent(s) and the diluent(s) is greater or less than about 0.19 g, but similarly stays the same independent of the concentration of the repellent. With different sets of experiments, the amount of skin-applied test substance used in the testing is based on the size of the substrate and the properties of different testing insect repellents, such as the active ingredient dosage. For example, the greater the surface area of the substrate, the larger the amount of test substance that is used during the testing.

Moreover, during step 310, another similarly warmed substrate 106 is treated with ethanol without any insect repellent. In step 312, the container 102 and the substrate from step 310 are placed in communication with one another and the mosquitoes are exposed to substrate 106. The number of mosquitoes that land on substrate 106 from step 310 for equal to or greater than about 2 seconds (i.e., a "bite") is recorded in step 314. Next, a query is undertaken at step 316. If the number recorded in step 314 is smaller than 20 in about 60 seconds, the mosquitoes will need to be replaced with new mosquitoes from the insectary cage at step 300. If the number recorded in step 314 is not less than 20 in about 60 seconds, the testing method will proceed to step 318, which requires removal of substrate 106 of step 310 from communication with container 102 and placing substrate 106 from step 308 into communication with the container 102 and exposing mosquitoes to substrate 106 for about 60 seconds.

During Step 318, the treated skin substitute substrate 106 is exposed to biting insects for a first time period of about X minutes, withdrawn from the biting insects for a second time period of about Y minutes, and subsequently exposed for the first time period of about X minutes to the biting insects again. This cycle of exposure-withdrawal-exposure is repeated until one or more biting insects land on the treated substrate for equal to or longer than 2 seconds. In an alternative embodiment, during step 318, the treated substrate is exposed to biting insects within a range of about 1 to about 5 minutes and withdrawn for a range of about 25 to about 29 minutes. Step 318 is repeated for n times (n≥1) until one or more mosquitoes land on the treated substrate 106 during the (n)th exposure and during the subsequent (n+1)th exposure. At step 320, exposure of mosquitoes to the treated substrate 106 is terminated and the time needed to obtain the first bite during the (n)th exposure is recorded as the CPT for measuring the efficacy of the skin-applied insect repellent. Collagen-based substrates do not hold up and cannot be used in such a multi-cycle testing protocol.

Figure 5:
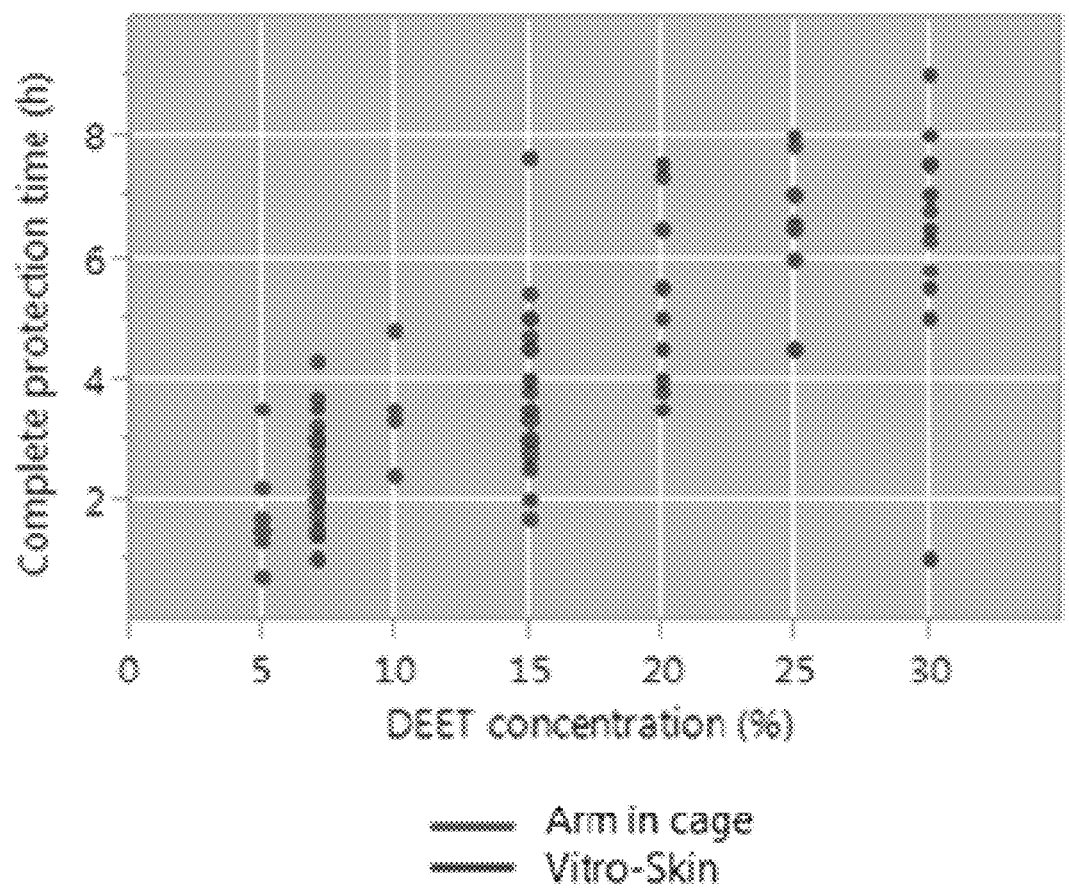
FIG. 5 is a scatter plot showing comparisons of complete protection time ("CPT") of N,N-Diethyl-3-methylbenzamide ("DEET") in hours for tests involving human participants and tests involving a human surrogate apparatus according to an embodiment of the present disclosure in a laboratory.

When comparing the CPT data of skin-applied insect repellents, such as DEET, using the human surrogate apparatus 100 to the CPT data of skin-applied insect repellents obtained using human research participants via the arm-in-cage method (See Product Performance Test Guidelines OPPTS 810.3700: Insect Repellents to be Applied to Human Skin, United States Environmental Protection Agency, EPA 712-10-001, Jul. 7, 2010), data from both groups is very similar to each other as may be seen with reference to FIG. 5 in a controlled environment, e.g., a laboratory. Further, Table 1 illustrates the average CPT for the two methods based on differing weight percentages of the active ingredient DEET of the insect repellent, as well as the standard deviation ("±SE") at each weight percentage for the two groups. As may be seen, the differences between the experiments using human research participants via the arm-in-cage method and the experiments using the human surrogate apparatus 100 are statistically negligible.

TABLE 1

Mean (±SE) and median CPT in hours for different concentrations of DEET in ethanol (EtOH) using the arm in cage method and human surrogate apparatus 100 method.

| Concentration (% DEET) | Complete protection time Mean ± SE (median) | |
|---|---|---|
| | Arm in cage | Human Skin Surrogate |
| 7 | 2.5 ± 0.7 (2.3) | 2.2 ± 0.9 (2.0) |
| 15 | 3.9 ± 1.5 (3.5) | 3.6 ± 1.0 (3.3) |
| 20 | 4.9 ± 2.1 (3.8) | 4.9 ± 2.1 (5.3) |
| 25 | 6.5 ± 1.4 (6.8) | 6.3 ± 1.1 (6.5) |
| 30 | 6.6 ± 0.7 (6.6) | 6.5 ± 2.3 (7.0) |

Figure 6:
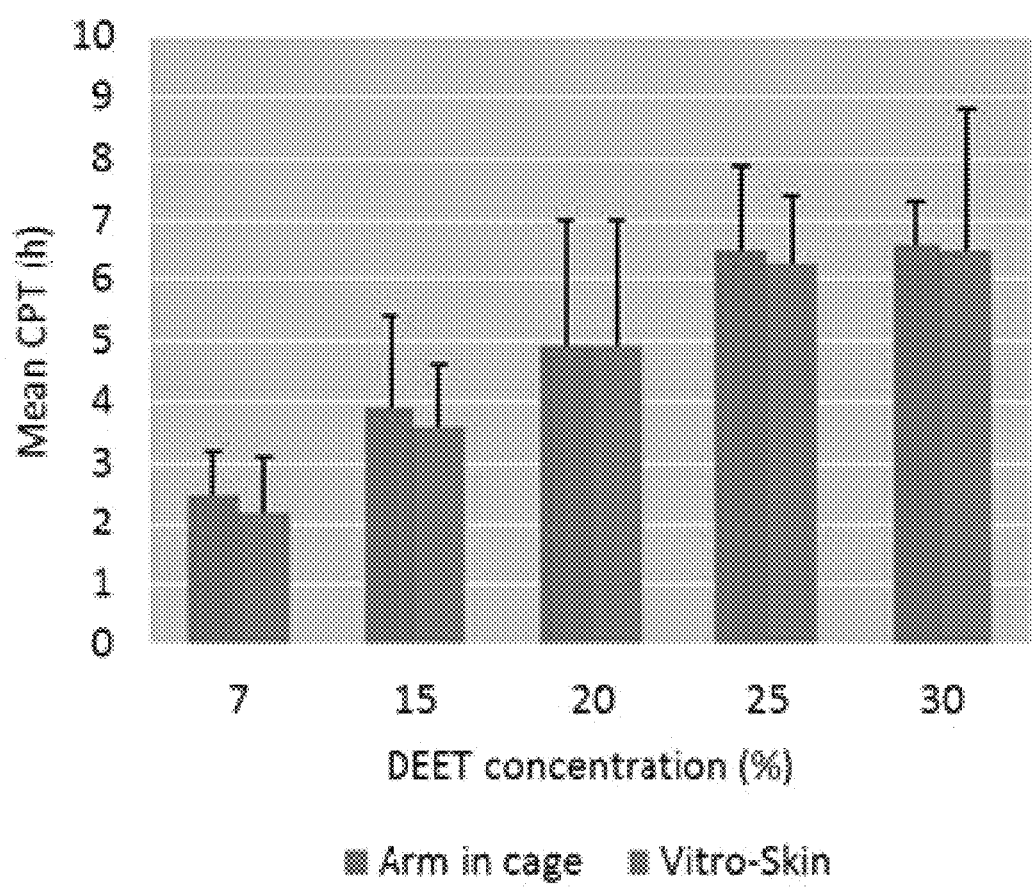
FIG. 6 is a bar graph showing comparisons of mean CPT in hours with different concentrations of DEET for tests involving human participants and tests involving a human surrogate apparatus according to an embodiment of the present disclosure.

With reference to FIG. 6, the mean CPT (±SE) between the two groups for testing different weight percentages of DEET in ethanol is displayed. Similarly, there is a statistically negligible difference between the experiments using human research participants via the arm-in-cage method and the experiments using the human surrogate apparatus 100.

Figure 7:
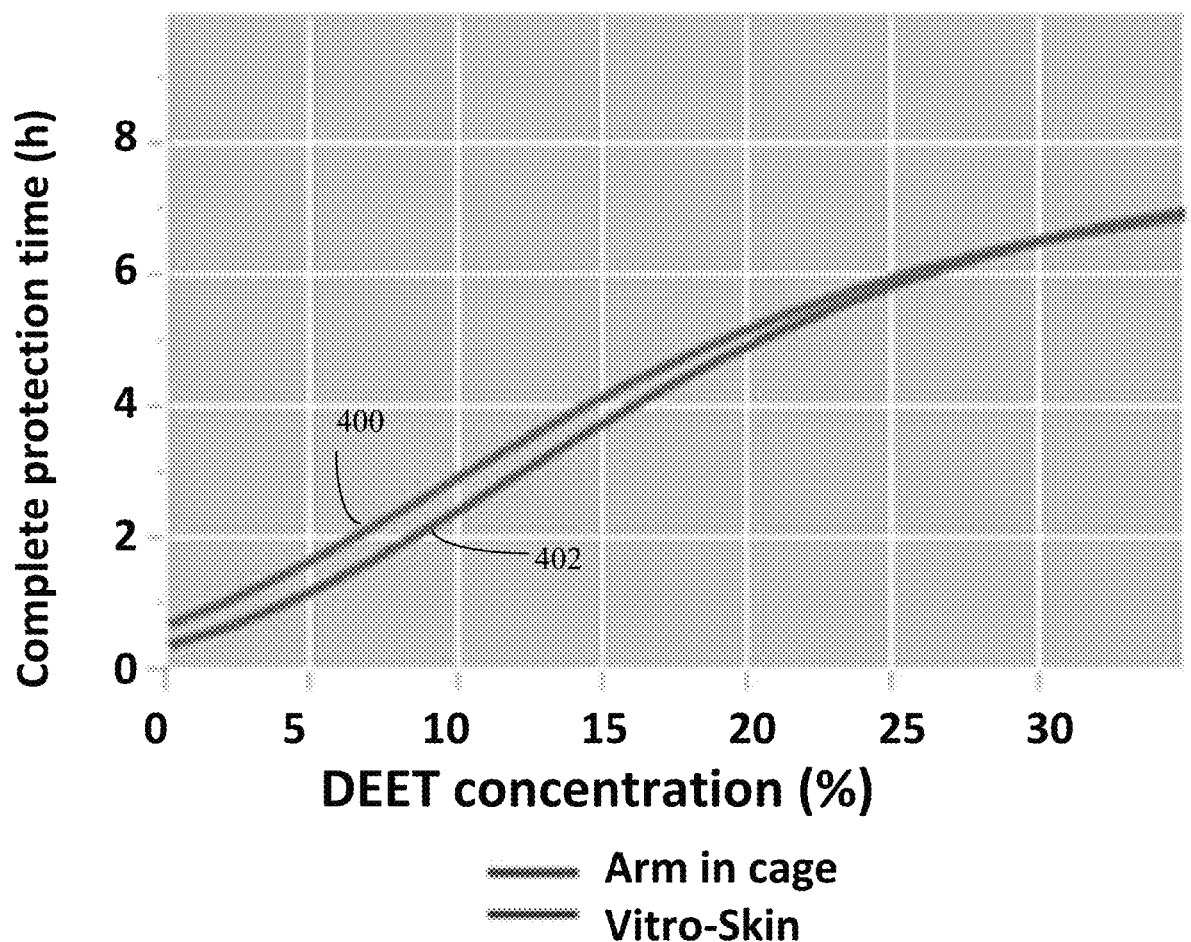
FIG. 7 is a graph comparing a selected mathematical model for CPT for tests involving human participants and tests involving a human surrogate apparatus according to an embodiment of the present disclosure.

Further, with reference to FIG. 7, comparison of five different non-linear, sigmoid models for the arm-in-cage method and the human surrogate apparatus 100 method have been performed and the best fit mathematical model for CPT is selected. Particularly, the model with the lowest corrected Akaike information criterion (AICc) and Bayesian information criterion (BIC) is selected as the model with the best fit to the data. Curve 400 of the arm-in-cage group demonstrates the CPT increases as the DEET concentration increases, and curve 402 of the human surrogate apparatus 100 group demonstrates a very similar correlation.

Moreover, when inversely predicting the average (±SE) weight percentage of DEET that corresponds to a given CPT in hours, the differences of the predicted weight percentages of DEET between the arm-in-cage group and the human surrogate apparatus 100 are minimal and statistically negligible, as may be seen in Table 2.

TABLE 2

Estimates are calculated for 1-6 h of complete protection time.

| Complete protection time (h) | Predicted percent DEET concentration (±SE) | |
|---|---|---|
| | Arm in cage | Human Skin Surrogate |
| 1 | 1.61 ± 1.69 | 3.81 ± 1.72 |
| 2 | 6.15 ± 0.94 | 8.17 ± 1.16 |
| 3 | 10.07 ± 0.88 | 11.92 ± 1.04 |
| 4 | 14.08 ± 1.15 | 15.71 ± 1.13 |
| 5 | 18.70 ± 1.46 | 20.00 ± 1.21 |
| 6 | 24.85 ± 2.64 | 25.55 ± 1.58 |

Figure 14:
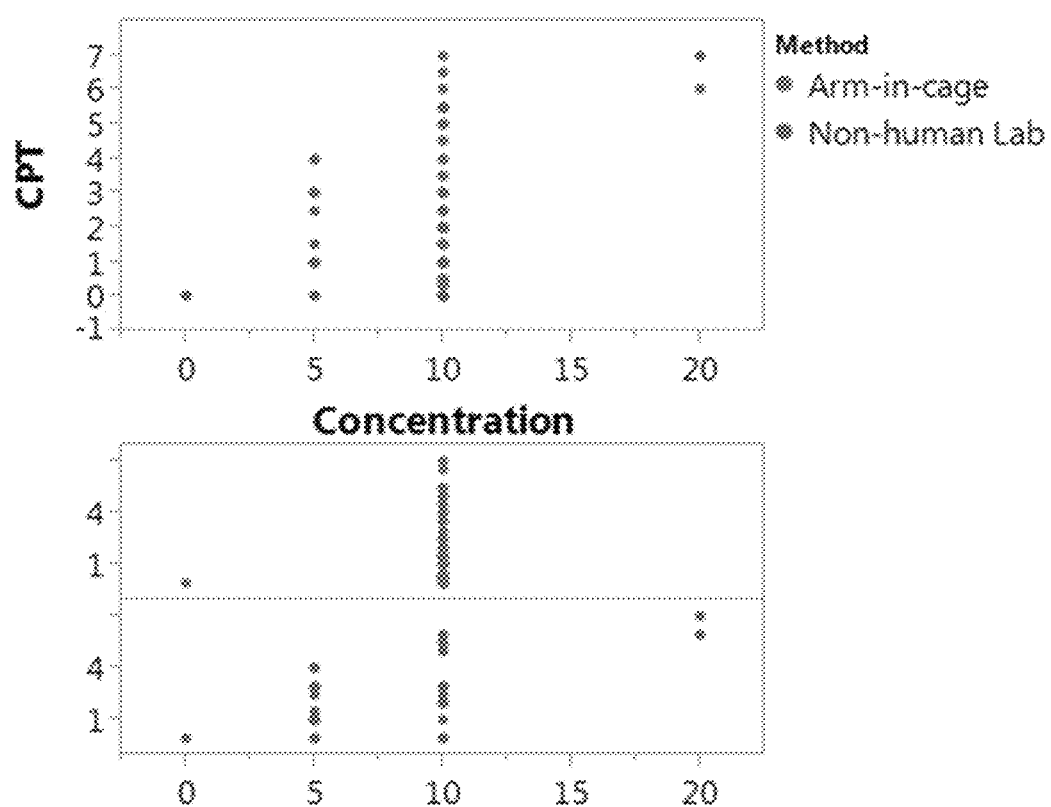
FIG. 14 illustrates a scatter plot showing comparisons of CPT of picaridin in hours for tests involving human participants and tests involving a human surrogate apparatus according to an embodiment of the present disclosure in a laboratory.
Figure 15:
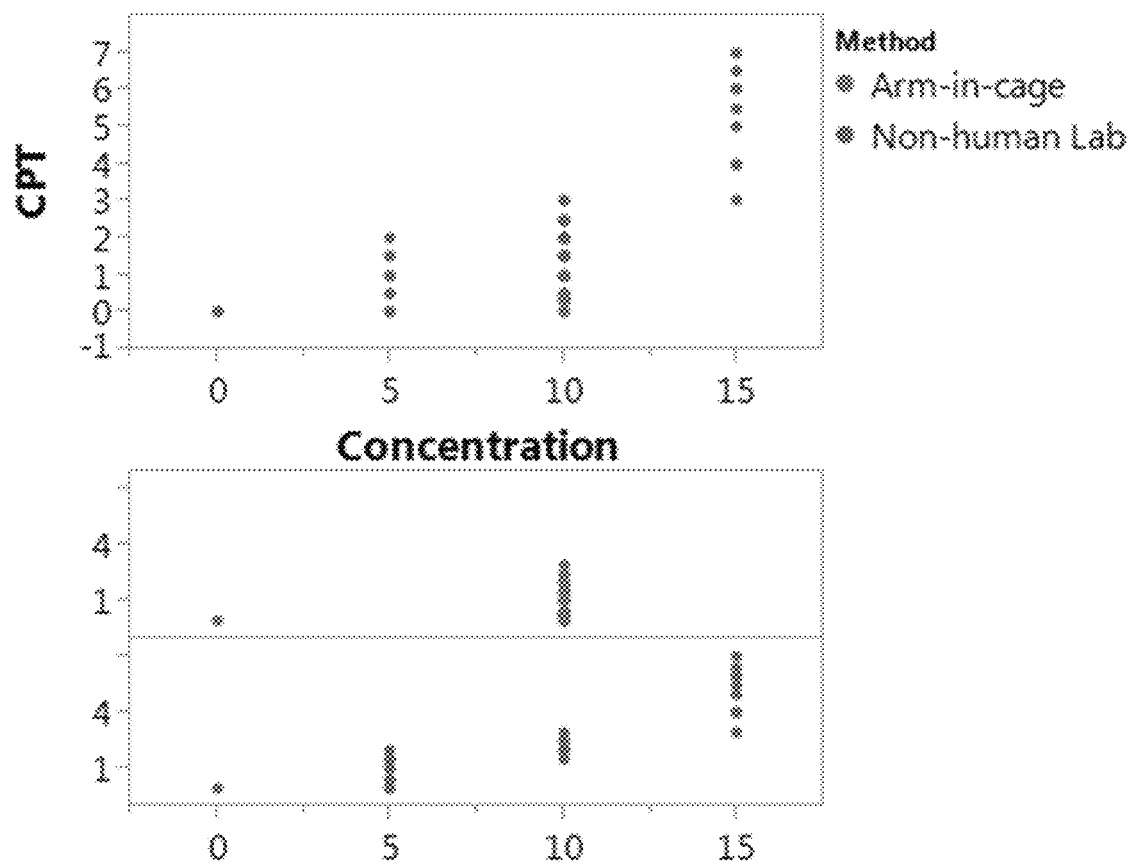
FIG. 15 illustrates a scatter plot showing comparisons of CPT of PMD in hours for tests involving human participants and tests involving a human surrogate apparatus according to an embodiment of the present disclosure in a laboratory.

Additionally, when other insect repellents are tested, such as picaridin and PMD, the CPT data obtained in the group using human surrogate apparatus 100 shares overlapping confidence intervals with, and is not significantly different from, the data obtained in the group using the arm-in-cage method in a laboratory. For example, referring to FIG. 14, the CPT data points at 10% by weight of picaridin of the group using human surrogate apparatus 100 are within the range of CPT data points of the group employing the arm-in-cage method. Similarly, referring to FIG. 15, the CPT data at 10% by weight of PMD of the human surrogate apparatus 100 group is not significantly different from the CPT data of the arm-in-cage group.

Figure 8:
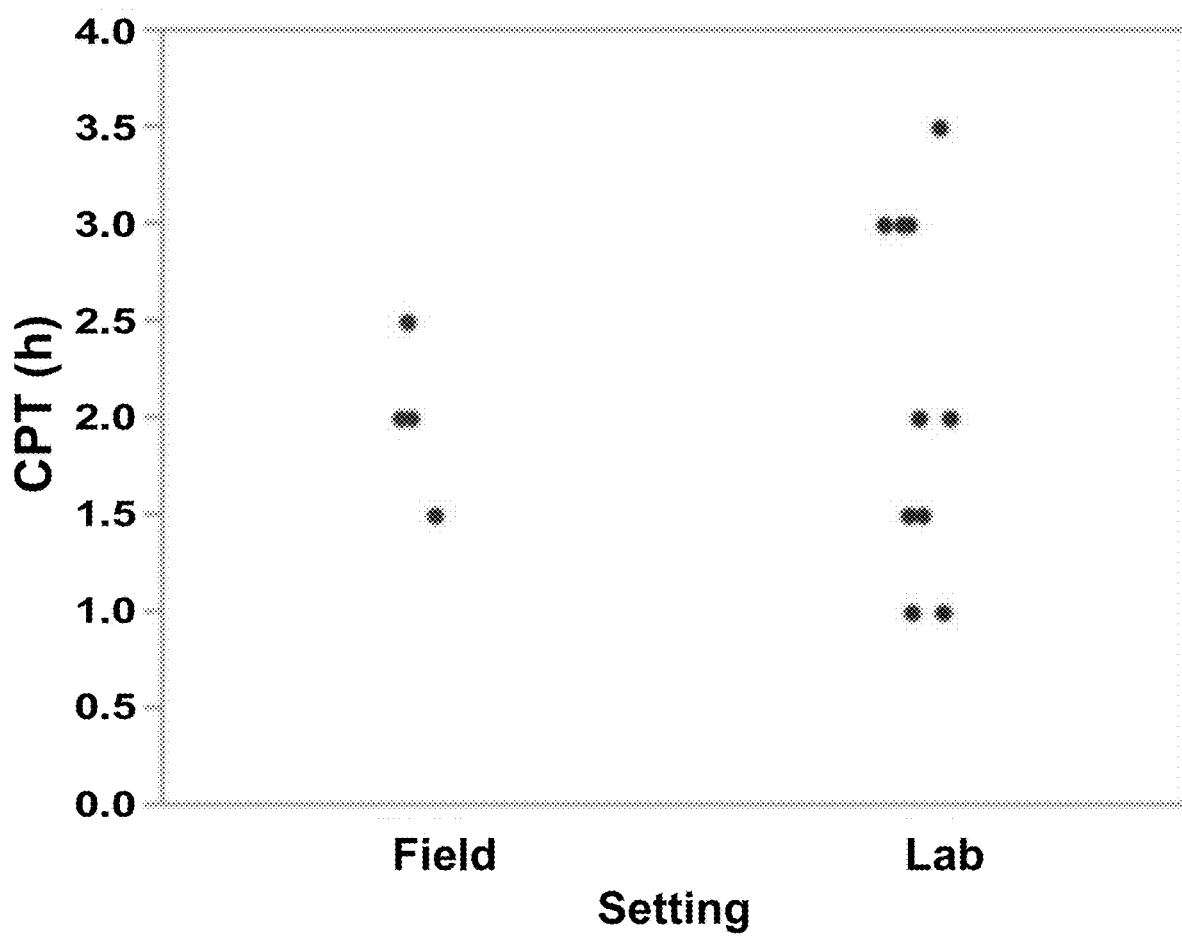
FIG. 8 is a scatter plot showing comparisons of CPT in hours for 7% DEET between laboratory and field tests using a human surrogate apparatus according to an embodiment of the present disclosure.

It has also been experimentally determined that the human surrogate apparatuses described herein perform consistently in a controlled environment, e.g., a laboratory with predetermined and controllable conditions, and in an uncontrolled environment, e.g., in an outdoor field test. With reference to FIG. 8 and Table 3, the CPT in hours obtained from testing 7% weight percentage DEET repellent efficacy in the laboratory and obtained from the field is similar. Therefore, utilization of either of the human surrogate apparatuses 100, 200 does not affect testing results.

TABLE 3

Mean (±SE), median, and range of CPT in hours conducted in the laboratory and field using 7% DEET in EtOH.

| | Complete protection time (h) | | |
|---|---|---|---|
| Setting | Mean ± SE | Median | Range |
| Field | 2.0 ± 0.4 | 2.0 | 1.5-2.5 |
| Lab | 2.2 ± 0.9 | 2.0 | 1.0-3.5 |

Figure 10A:
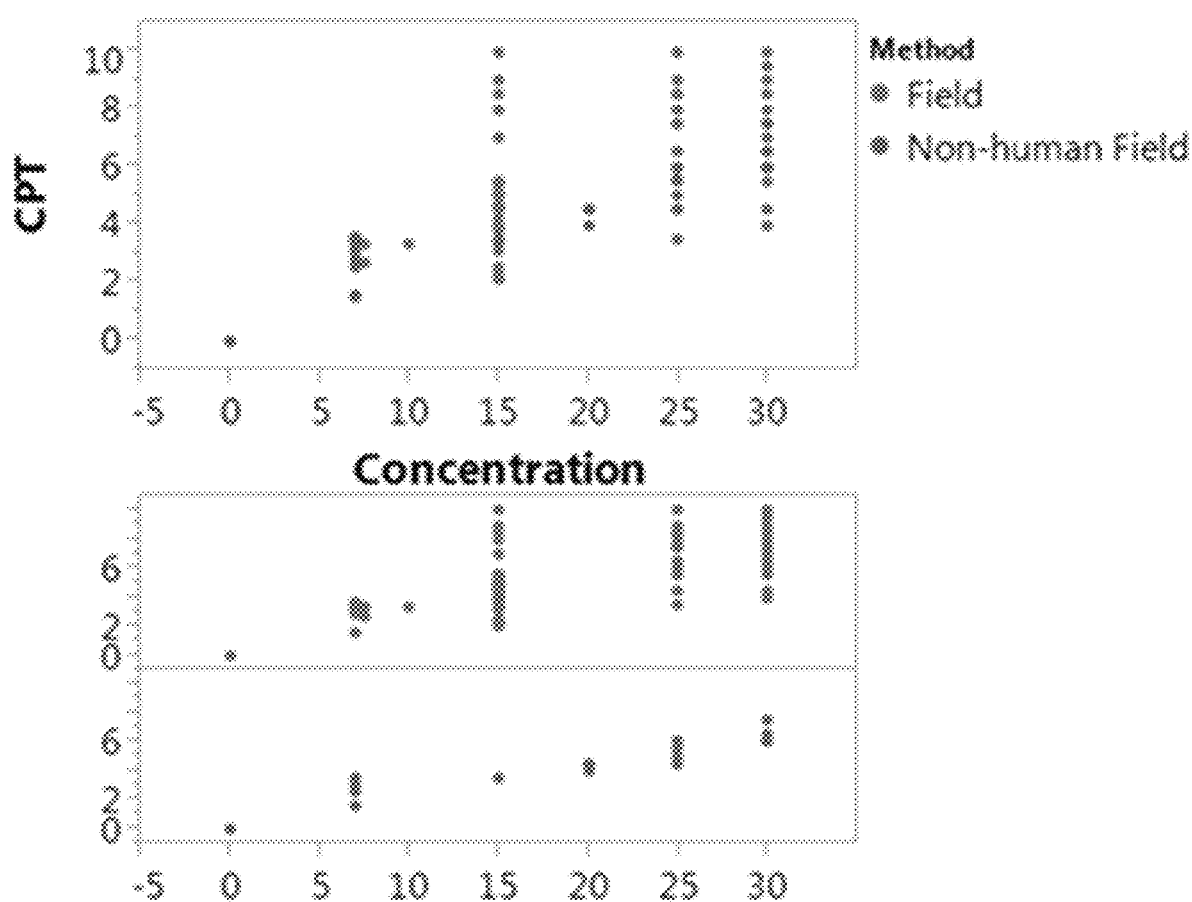
FIG. 10A is a scatter plot showing comparisons of CPT in hours of DEET in field tests involving human participants and a human surrogate apparatus according to an embodiment of the present disclosure.
Figure 10B:
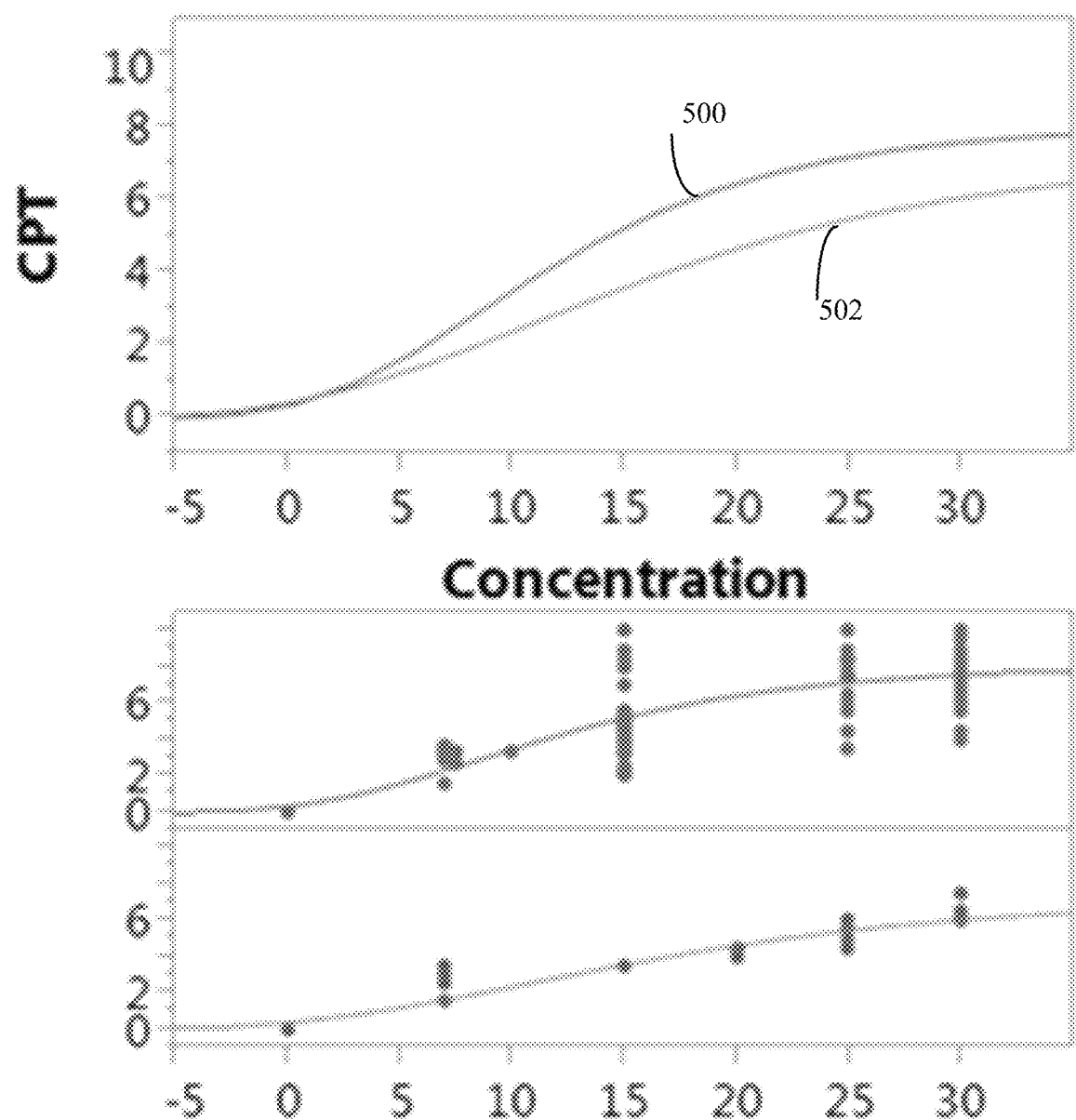
FIG. 10B is a graph comparing a selected mathematical model for CPT for tests conducted in FIG. 10A.
Figure 10C:
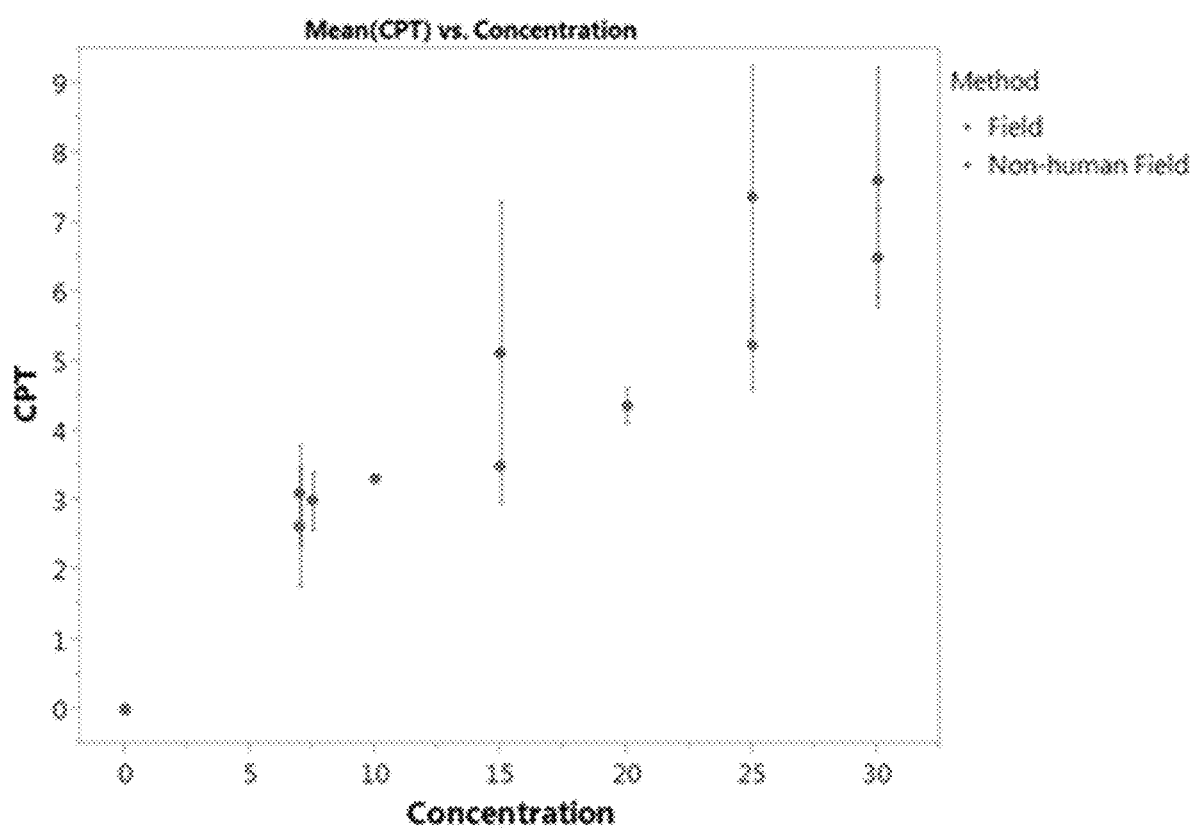
FIG. 10C shows comparisons of mean CPT in hours from FIG. 10A.
Figure 11A:
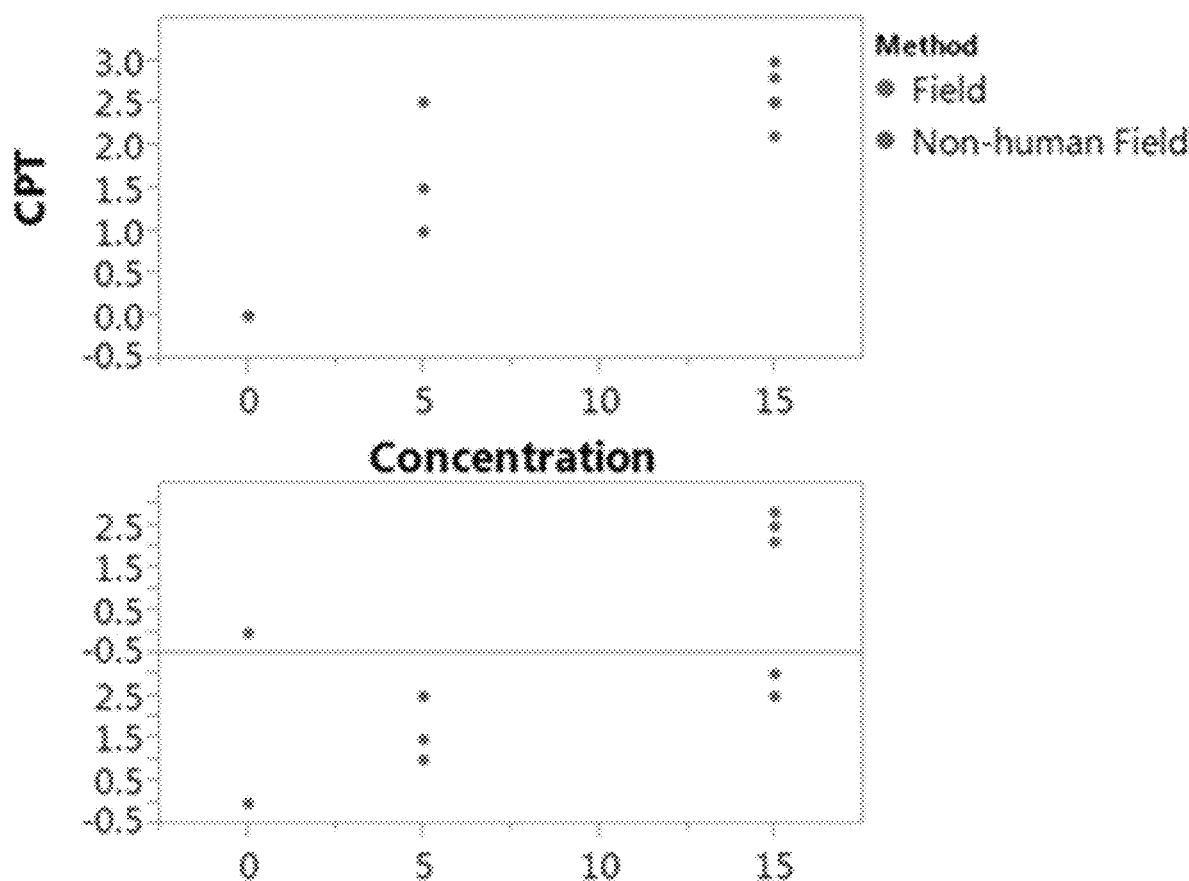
FIG. 11A is a scatter plot showing CPT in hours of 2-(2-hydroxyethyl)-1-piperidinecarboxylic acid 1-methylpropyl ester (picaridin) for field tests involving human participants and a human surrogate apparatus according to an embodiment of the present disclosure.
Figure 11B:
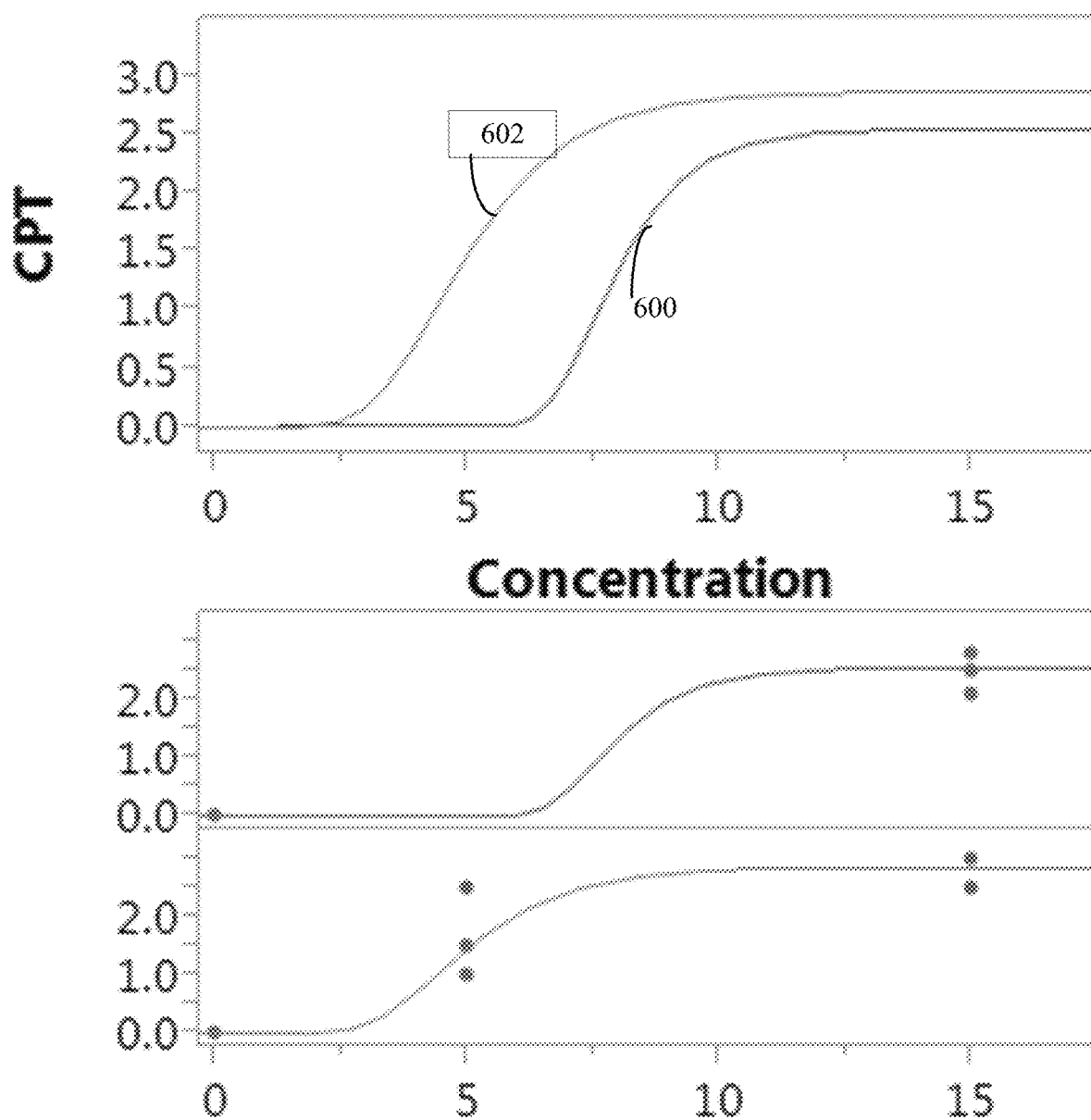
FIG. 11B is a graph comparing a selected mathematical model for CPT for tests conducted in FIG. 11A.
Figure 11C:
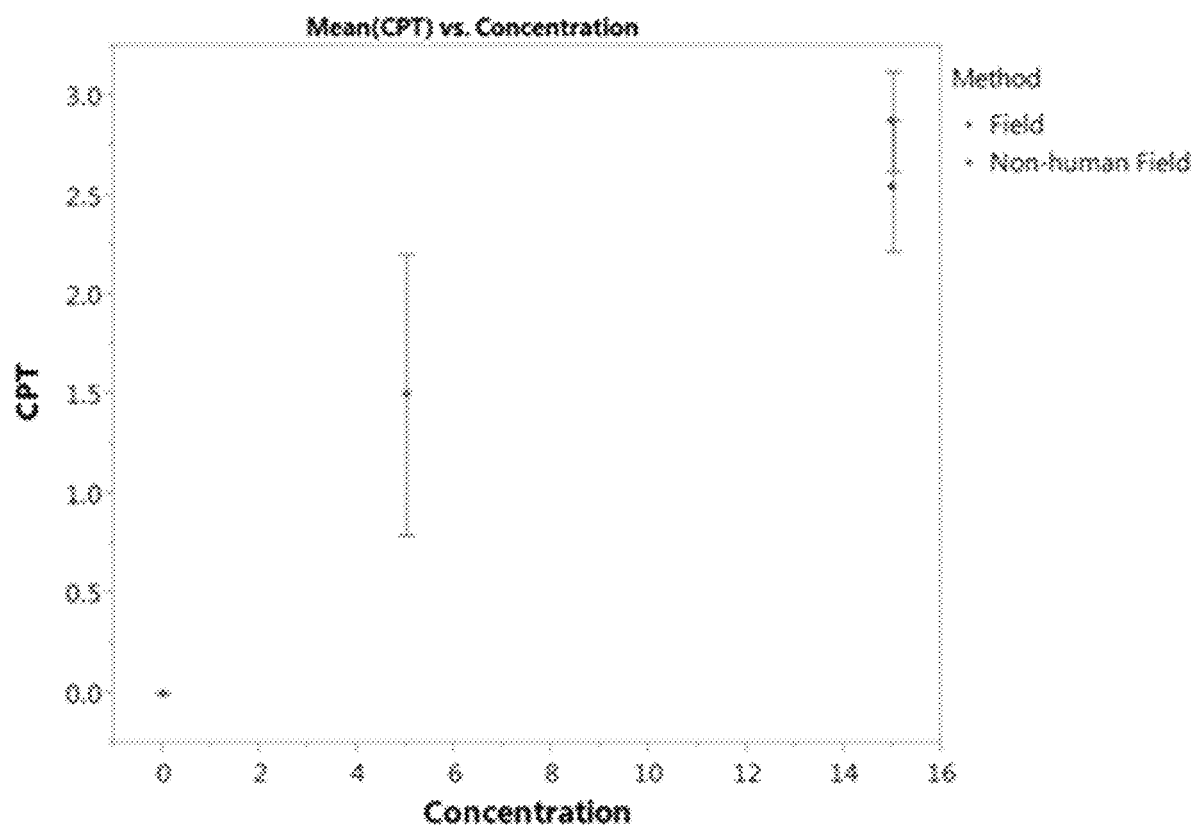
FIG. 11C shows comparisons of mean CPT in hours from FIG. 11A.
Figure 12A:
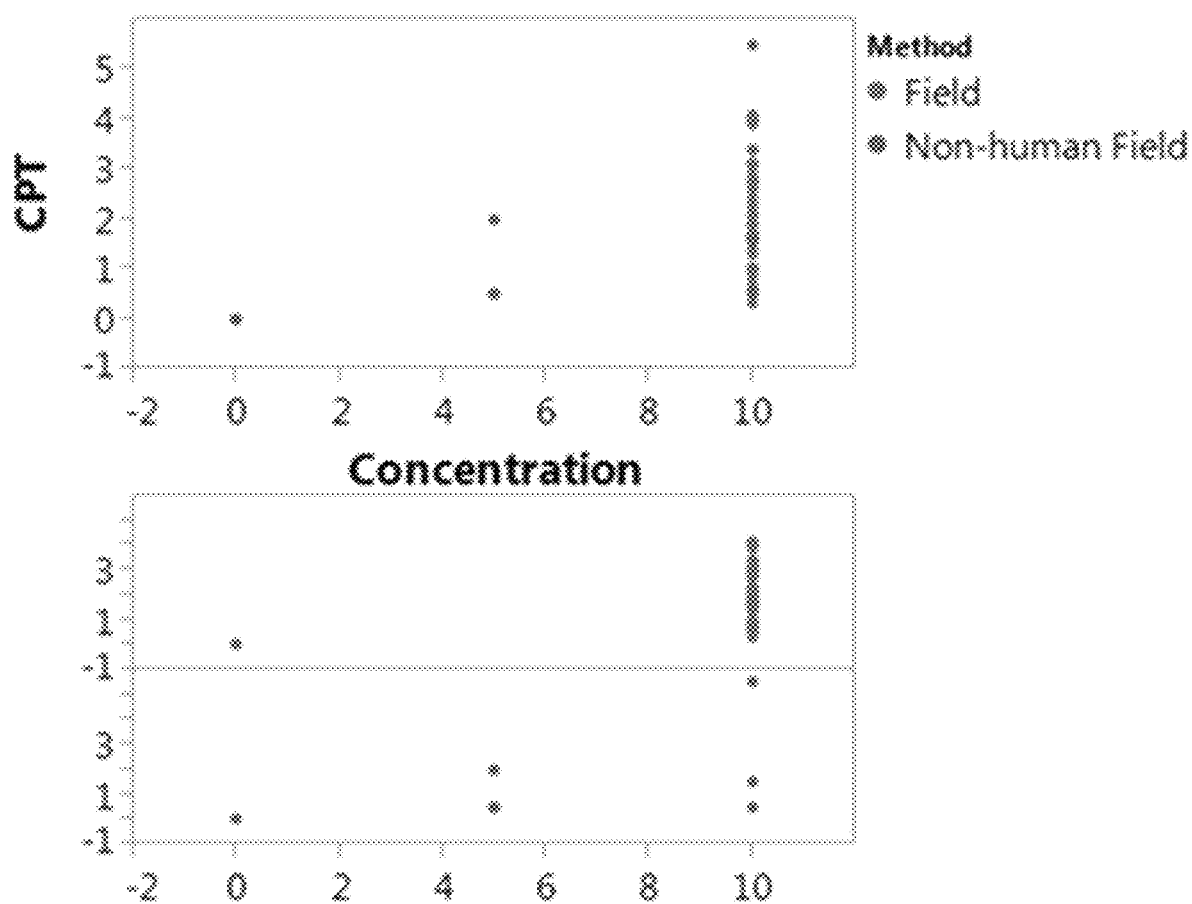
FIG. 12A is a scatter plot showing CPT in hours of para-menthane-3,8-diol (PMD) for field tests involving human participants and a human surrogate apparatus according to an embodiment of the present disclosure.
Figure 12B:
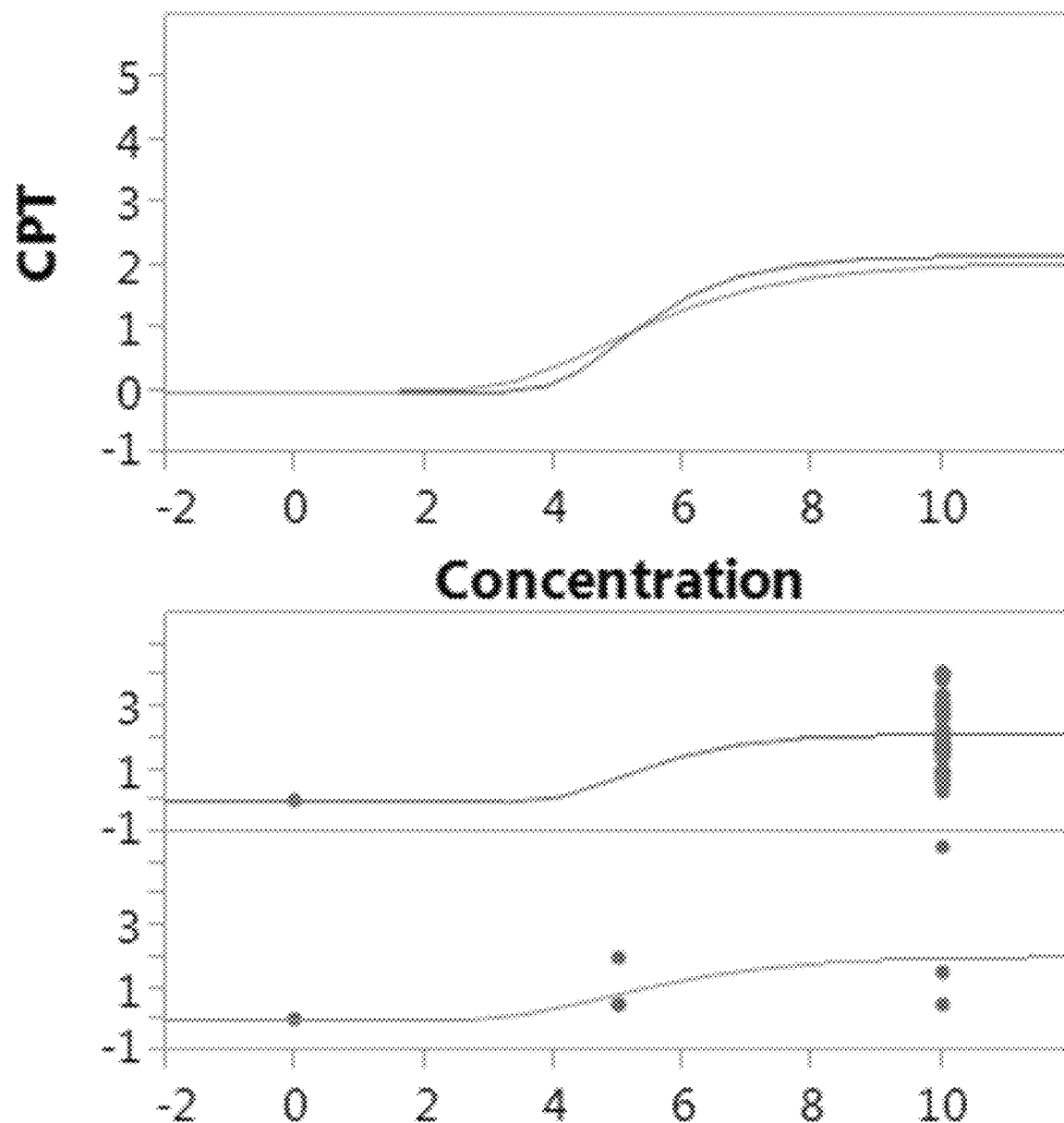
FIG. 12B is a graph comparing a selected mathematical model for CPT for tests conducted in FIG. 12A.
Figure 12C:
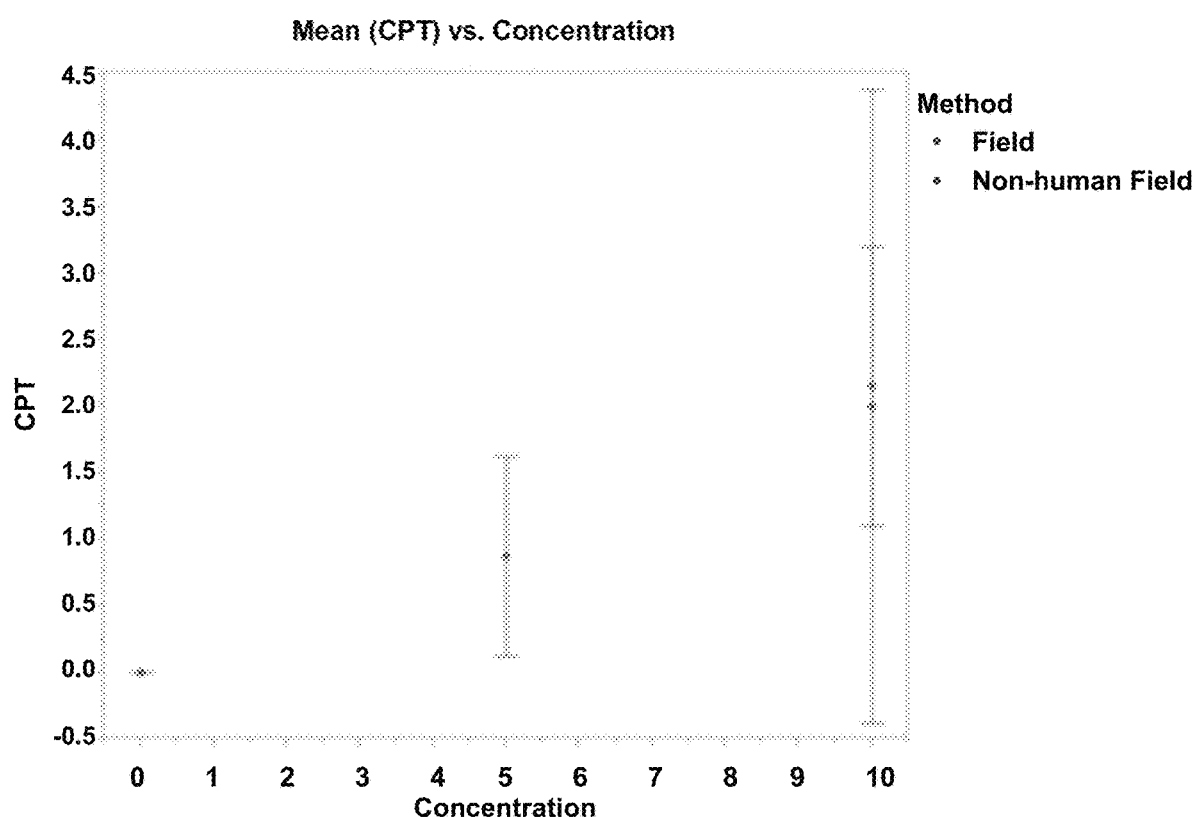
FIG. 12C shows comparisons of mean CPT in hours from FIG. 12A.

The CPT data of skin-applied insect repellents using human surrogate apparatus 200 and the CPT data of skin-applied insect repellents obtained using voluntary human research participants outdoor (please refer to OPPTS 810.3700. Insect repellents for human skin and outdoor premises at https://rchive.epa.gov/scipoly/sap/meetings/web/pdf/insectguid.pdf for outdoor field test protocols) are comparable. For example, referring to FIGS. 10A-10C, the CPT data (including average CPT) of DEET in the human surrogate apparatus 200 group shares overlapping confidence intervals with the CPT data in the field test group using voluntary human subjects, i.e., the CPT data in the human surrogate apparatus 200 group is not significantly different from the CPT data in the voluntary human subjects group. Further, referring to FIG. 10B, curve 500 of the voluntary human subjects group demonstrates the CPT increases as the DEET concentration increases in the field and curve 502 of the human surrogate apparatus 200 group demonstrates a very similar correlation. Similarly, for testing substance picaridin (referring to FIGS. 11A-11C) and PMD (referring to FIGS. 12A-12C), the CPT data (including average CPT) in the human surrogate apparatus 200 group shares overlapping confidence intervals with the CPT data in the field test group using the voluntary human subjects. No statistically significant difference is observed in either the picaridin outdoor field test or the PMD outdoor field test when comparing groups involving human participants to groups involving the human surrogate apparatuses.

Figure 13:
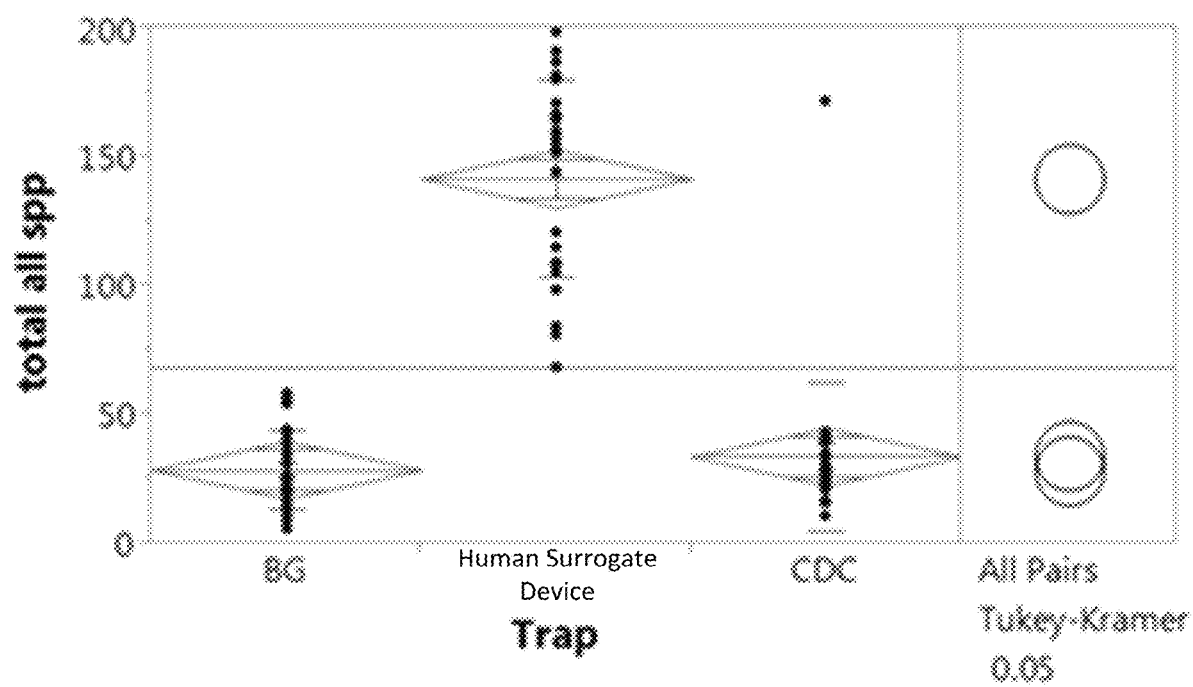
FIG. 13 shows numbers of mosquitoes that landed on the skin substitute substrate when using a human surrogate apparatus according to an embodiment of the present disclosure and numbers of mosquitoes trapped by industry-standard mosquito traps in the field.

The human surrogate apparatus can also be used in evaluating mosquito landing pressure (also known as landing frequency), which represents mosquitoes' intent to bite according to the EPA. In certain embodiments, human surrogate apparatus 200 is utilized in recording the number of wild mosquitoes that land on the human surrogate apparatus during a period of time. Referring to FIG. 13 and Table 4, the number of mosquitoes reported for the human surrogate apparatus, which is the number of mosquitoes that landed on the apparatus over a 1-minute period, was significantly higher than the numbers of mosquitoes captured by the industry standard mosquito traps, such as the CDC Miniature Light Trap (http://johnwhock.com/products/mosquito-sandfly-traps/cdc-miniature-light-trap/) and the BG Sentinel-2 trap (Biogents, http://www.biogents.com/bg-sentinel/) over a one hour period. In FIG. 13, "total all spp" is the total number of mosquitoes of all species captured by the CDC or BG trap or that landed on the human surrogate apparatus. Due to the human surrogate apparatus' ability to record landings, a capture step is not necessary, making the human surrogate apparatus a better indicator of mosquito activity in a given area. Gathering mosquito activity in an area is very important in determining potential for disease transmission, etc.

TABLE 4

Summary statistics

| Device | Mean number of mosquitoes |
|---|---|
| Non-human device | 141.7* |
| CDC Miniature Light Trap | 33.8** |
| BG Sentinel-2 | 28.7** |

*Number of mosquito lands over a 1-minute period
**Number of mosquitoes captured over a 1-hour period Industry-standard mosquito traps are not ideal for evaluating mosquitoes landing pressure in an outdoor setting because mosquitoes have to pass through certain barriers of the traps, whereas, using voluntary human subjects in a similar evaluation would not require mosquitoes to pass through any barriers. However, as aforementioned, there are several disadvantages associated with using voluntary human subjects. Based on the results demonstrated in FIG. 13 and table 4, the human surrogate apparatus disclosed in the current application is ideal to replace voluntary human subjects in evaluating mosquitoes landing pressure and biting pressure (also known as biting frequency).

Any of the embodiments described herein may be modified to include any of the structures or methodologies disclosed in connection with different embodiments.

INDUSTRIAL APPLICABILITY

A human surrogate apparatus for testing the efficacy of a skin-applied insect repellent is presented that is comparable in results to testing involving human participants.

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved.

We claim:
1. An apparatus, comprising:
a housing comprising an aperture extending through a wall of the housing;
a carbon dioxide delivery device coupled to the housing through the aperture;
a non-biological skin substitute substrate; and
a heater coupled to the non-biological skin substitute substrate,
wherein the non-biological skin substitute substrate has an Ra value of about 0.01 to about 0.2 µm.
2. The apparatus of claim 1, wherein the non-biological skin substitute substrate simulates at least one physical, chemical, or biological characteristic of human skin.
3. The apparatus of claim 2, wherein the non-biological skin substrate is synthetic.
4. The apparatus of claim 2, wherein the non-biological skin substitute substrate has specular reflectance peak at a wavelength of about 306 nm.
5. The apparatus of claim 2, wherein the non-biological skin substitute substrate exhibits Lambertian reflectance.

* * * * *